(12) United States Patent
Amanullah et al.

(10) Patent No.: US 10,472,958 B2
(45) Date of Patent: Nov. 12, 2019

(54) DETERMINING SPOTTING FLUID PROPERTIES

(71) Applicant: Saudi Arabian Oil Company, Dhahran (SA)

(72) Inventors: Md Amanullah, Dhahran (SA); Turki Thuwaini Mohammed Alsubaie, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/132,250

(22) Filed: Sep. 14, 2018

(65) Prior Publication Data

US 2019/0017376 A1    Jan. 17, 2019

Related U.S. Application Data

(63) Continuation of application No. 15/050,916, filed on Feb. 23, 2016.
(Continued)

(51) Int. Cl.
*G01N 19/04* (2006.01)
*E21B 49/00* (2006.01)
*G01L 25/00* (2006.01)

(52) U.S. Cl.
CPC .......... *E21B 49/003* (2013.01); *E21B 49/005* (2013.01); *G01L 25/00* (2013.01); *G01N 19/04* (2013.01)

(58) Field of Classification Search
None
See application file for complete search history.

(56) References Cited

U.S. PATENT DOCUMENTS 3,410,797 A    11/1968  Walker et al.
4,458,528 A     7/1984  Roper et al.
(Continued)

FOREIGN PATENT DOCUMENTS

EP    1137936    7/2003
FR    2758185    7/1998
(Continued)

OTHER PUBLICATIONS

Bushnell-Watson et al., "Differential Sticking Laboratory Tests can Improve Mud Design", SPE 22549, Copyright 1991, 10 pages.
(Continued)

*Primary Examiner* — Lisa M Caputo
*Assistant Examiner* — Jamel E Williams
(74) *Attorney, Agent, or Firm* — Fish & Richardson P.C.

(57) ABSTRACT

Techniques for determining properties of a spotting fluid include positioning a member of a test apparatus into a prepared mudcake sample at a specified depth, the mudcake sample associated with a drilling fluid and including a specified thickness; circulating a flow of the spotting fluid to contact the prepared mudcake sample in a test cell; soaking the prepared mudcake sample in the spotting fluid for a specified time duration; subsequent to the specified time duration, detecting a force exerted on the member relative to a displacement distance of the member from the specified depth in the mudcake sample during removal of the member from the mudcake sample; recording, with the test apparatus, the detected force relative to the displacement distance; and determining, with the test apparatus, one or more properties associated with the mudcake sample based on the recorded force relative to the displacement distance.

30 Claims, 13 Drawing Sheets

Related U.S. Application Data

(60) Provisional application No. 62/131,048, filed on Mar. 10, 2015.

(56) References Cited

U.S. PATENT DOCUMENTS

| | | | |
|---|---|---|---|
| 4,491,181 | A | 1/1985 | Krol |
| 4,829,816 | A | 5/1989 | Hubbard |
| 5,052,219 | A | 10/1991 | Fery |
| 5,260,268 | A | 11/1993 | Hubbard |
| 5,637,795 | A | 6/1997 | Hale et al. |
| 5,676,213 | A | 10/1997 | Auzerais |
| 6,267,186 | B1 | 7/2001 | Hayatdavoudi |
| 2007/0125158 | A1 | 6/2007 | Kelleher |
| 2010/0292107 | A1 | 11/2010 | Rayborn |
| 2014/0174168 | A1 | 6/2014 | Amanullah et al. |
| 2016/0266030 | A1 | 9/2016 | Amanullah |

FOREIGN PATENT DOCUMENTS

| | | |
|---|---|---|
| GB | 2275342 | 8/1994 |
| WO | 2014/098219 | 6/2014 |
| WO | 2016/144700 | 9/2016 |

OTHER PUBLICATIONS

Clark et al., "Evaluation of Spotting Fluids in a Full-Scale Differential-Pressure Sticking Apparatus", Society of Petroleum Engineers, Jun. 1992, 9 pages.

Amanulla, Md.; "Experimental Determination of Adhesive-Cohesive Bond Strength (ACBS) and Adhesion-Cohesion Modulus (ACM) of Mudcakes"; IDAC/SPE 77198 Asia Pacific Drilling Technology; Jan. 1, 2002; pp. 1-14.

Amanulla, Md.; "Experimental Determination of Compressive, Pulling and Torsional Resistance of Mudcakes using a Triple Action Load Cell Assembly"; South Afican Institute of Mining and Metallurgy; CSIRO Petroleum, Australia; ISRM 2003—Technology Roadmap for Rock Mechanics; Jan. 1, 2003; pp. 29-32.

Amanullah, Md.; "Method and Appartus to Reduce the Probability of Differential Sticking"; IADC/SPE-180506-MS, Asia Pacific Drilling Technology Conference; Aug. 22-24, 2016; pp. 1-15.

Engelhardt, "Filter Cake Formation and Water Losses in Deep Drilling Muds," 1954, State of Illinois; 31 pages.

Fann, Instruction Manual No. 100020420, Revision D, May 2014; 54 pages.

Merriam Webster, definition of "Spherical," Apr. 22, 2009.

Sherwood, "Differential Pressure Sticking of Drill String," AIChE Journal, vol. 44, No. 3, Mar. 1998, 11 pages.

International Search Report and Written Opinion of the International Searching Authority issued in International Application No. PCT/US2016/020710 dated Jun. 1, 2016; 12 pages.

International Search Report and Written Opinion of the International Searching Authority issued in International Application No. PCT/US2017/016123 dated Mar. 10, 2017; 13 pages.

Gulf Cooperation Council Examination Report issued in GCC Application No. GC 2016-30950 dated May 31, 2018, 6 pages.

Gulf Cooperation Council Examination Report issued in GCC Application No. GC 2016-30950 dated Oct. 13, 2018, 3 pages.

Gulf Cooperation Council Examination Report issued in GCC Application No. GC 2016-32972 dated Dec. 28, 2018, 4 pages.

Gulf Cooperation Council Examination Report issued in GCC Application No. GC 2016-30950 dated Feb. 12, 2019, 4 pages.

Gulf Cooperation Council Examination Report issued in GCC Application No. GC 2017-32972 dated Mar. 25, 2019, 4 pages.

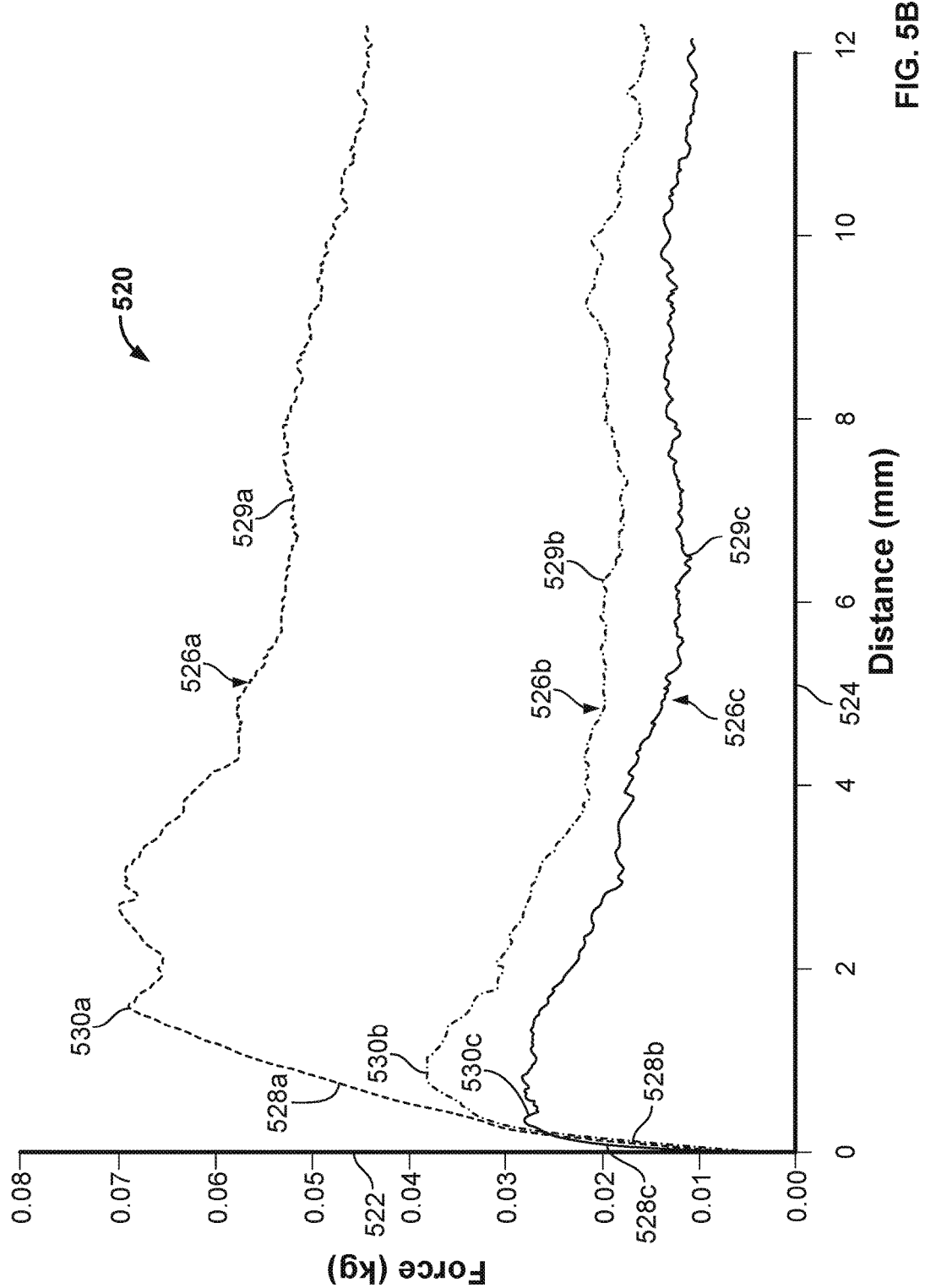

DETERMINING SPOTTING FLUID PROPERTIES

CROSS-REFERENCE TO RELATED APPLICATION

This application is a continuation of, and claims priority under 35 U.S.C. § 120 to, U.S. patent application Ser. No. 15/050,916, filed on Feb. 23, 2016, and entitled "Determining Spotting Fluid Properties," which in turn claims priority under 35 U.S.C. § 119 to U.S. Provisional Patent Application Ser. No. 62/131,048, filed on Mar. 10, 2015, and entitled "Determining Mudcake Properties," the entire contents of each previous application are incorporated herein by reference.

TECHNICAL FIELD

This disclosure relates to methods and systems for determining one or more properties of a spotting fluid for use in a wellbore.

BACKGROUND

Tubular members, such as drill pipe or otherwise, can often become stuck in a wellbore during drilling or other operations, often referred to a "pipe sticking." Pipe sticking can be a problem in the drilling and formation of wellbores that can cause non-productive drilling time. Pipe sticking can also trigger other drilling problems and sometimes may lead to a costly fishing operation to retrieve the stuck tubular, abandonment of the operation, or side tracking of the wellbore. Because of these costly problems, conventional techniques have been developed to predict pipe sticking in advance, for example, by evaluating properties related to an interface in a drilling mud and the tubular in the wellbore. The drilling mud, when in contact with a rock formation of the wellbore, may develop a mudcake (for example, drilling fluid that attaches to the wellbore under pressure). Conventional techniques, however, that are used to determine sticking or adherence properties of a mudcake to a rigid tubular (for example, a metallic drilling string) are often not reliable or accurate.

A fluid (for example, a liquid) may be used during a pipe unsticking operation in the wellbore. The fluid, typically called a "spotting fluid," may help unstick the pipe from the wellbore. But as with mudcakes, conventional techniques that are used to determine sticking or adherence properties of a spotting fluid for freeing a rigid tubular (for example, a metallic drilling string) are often not reliable or accurate.

SUMMARY

This disclosure describes implementations of methods and systems for determining one or more properties associated with an adherence or sticking of a mudcake to a wellbore tubular member. In example implementations, testing methods and systems include preparing and testing a mudcake sample. The mudcake sample is prepared to a particular thickness, for example, at least 10 millimeters (mm), and placed in a mudcake testing system. The mudcake testing system is operated by a control system to embed a test member (for example, a spherical foot) into the mudcake sample and remove the embedded test member while recording removal force and removal displacement data. The recorded data is used to determine one or more mechanical properties of the mudcake sample, which, in turn, may be used to, for instance, make decisions on drilling fluid selection and other wellsite operations.

In an example implementation, a method includes positioning a member of a test apparatus into a prepared mudcake sample at a specified depth of the mudcake sample, the mudcake sample associated with a drilling fluid and including a specified thickness; detecting, with the test apparatus, a force exerted on the member relative to a displacement distance of the member from the specified depth in the mudcake sample during removal of the member from the mudcake sample; recording, with the test apparatus, the detected force relative to the displacement distance; and determining, with the test apparatus, one or more properties of the mudcake sample based on the recorded force relative to the displacement distance.

A first aspect combinable with the example implementation further includes preparing the mudcake sample to the specified thickness.

A second aspect combinable with any of the previous aspects further includes initiating removal of the member from the mudcake sample by the force exerted on the member by the test apparatus.

In a third aspect combinable with any of the previous aspects, the specified thickness is at least 10 mm.

In a fourth aspect combinable with any of the previous aspects, the specified depth is half of the specified thickness.

In a fifth aspect combinable with any of the previous aspects, the specified thickness is 10 mm and the specified depth is 5 mm.

A sixth aspect combinable with any of the previous aspects further includes removing the member from the mudcake sample by the force exerted on the member by the test apparatus.

In a seventh aspect combinable with any of the previous aspects, removing the member from the mudcake sample by the force exerted on the member by the test apparatus includes removing the member from the mudcake sample at a constant removal rate.

In an eighth aspect combinable with any of the previous aspects, removing the member from the mudcake sample by the force exerted on the member by the test apparatus includes removing the member from the mudcake sample in a linear direction.

A ninth aspect combinable with any of the previous aspects further includes maintaining, for a specified time duration, the member in the mudcake sample prior to initiating removal of the member from the mudcake sample.

In a tenth aspect combinable with any of the previous aspects, the specified time duration includes 2 minutes.

In an eleventh aspect combinable with any of the previous aspects, the member includes a spherical member.

In a twelfth aspect combinable with any of the previous aspects, preparing the mudcake sample includes preparing the mudcake sample using an American Petroleum Institute (API) or a high pressure high temperature (HTHP) test apparatus.

In a thirteenth aspect combinable with any of the previous aspects, preparing the mudcake sample includes filtering the mudcake sample for a specified time duration.

In a fourteenth aspect combinable with any of the previous aspects, filtering the mudcake sample for a specified time duration includes filtering the mudcake sample from between one hour and 48 hours.

In a fifteenth aspect combinable with any of the previous aspects, the mudcake sample includes one of: a bentonite drilling fluid, a bentonite-salt drilling fluid, a potassium chloride polymer, or a low solids non-dispersed (LSND) drilling fluid.

In a sixteenth aspect combinable with any of the previous aspects, one or more properties of the mudcake sample include a sticking bond modulus (SBM) and an ultimate sticking bond strength (USBS).

A seventeenth aspect combinable with any of the previous aspects further includes graphically recording the force exerted on the member relative to the displacement distance.

An eighteenth aspect combinable with any of the previous aspects further includes determining at least one of the one or more properties based, at least in part, on the graphical recording of the force exerted on the member relative to the displacement distance.

In a nineteenth aspect combinable with any of the previous aspects, the graphical recording of the force exerted on the member relative to the displacement distance includes a linear portion and a non-linear portion.

A twentieth aspect combinable with any of the previous aspects further includes determining the SBM of the mudcake sample based on a slope of the non-linear portion of the graphical recording of the force exerted on the member relative to the displacement distance.

A twenty-first aspect combinable with any of the previous aspects further includes determining the USBS of the mudcake sample based on a peak exerted force value of the graphical recording of the force exerted on the member relative to the displacement distance.

A twenty-second aspect combinable with any of the previous aspects further includes selecting a drilling fluid for a drilling operation based, at least in part, on one or more of the determined properties.

A twenty-third aspect combinable with any of the previous aspects further includes selecting an additive for a drilling fluid for a drilling operation based, at least in part, on one or more of the determined properties.

A twenty-fourth aspect combinable with any of the previous aspects further includes determining an ease of recovery of a tubular member that is stuck in a wellbore based, at least in part, on one or more of the determined properties.

A twenty-fifth aspect combinable with any of the previous aspects further includes performing at least one step of the method at a wellsite location.

In another example implementation, a mudcake testing system includes a test apparatus including: a mudcake holder configured to restrain the mudcake sample in a stationary position, a load cell, and a testing member coupled to the load cell; and a control system communicably coupled to the test apparatus and configured to perform operations including: controlling the load cell to position the member into the mudcake sample at a specified depth of the mudcake sample; controlling the load cell to initiate removal of the member from the mudcake sample by a force exerted on the member by the load cell; detecting, with the test apparatus, a force exerted on the member relative to a displacement distance of the member from the specified depth in the mudcake sample during removal of the member from the mudcake sample; recording, with the test apparatus, the detected force relative to the displacement distance; and determining one or more properties of the mudcake sample based on the recorded force relative to the displacement distance.

A first aspect combinable with the example implementation further includes a mudcake preparation assembly configured to prepare a mudcake sample associated with a drilling fluid, the mudcake sample including a specified thickness;

In a second aspect combinable with any of the previous aspects, the specified thickness is at least 10 mm.

In a third aspect combinable with any of the previous aspects, the specified depth is half of the specified thickness.

In a fourth aspect combinable with any of the previous aspects, the specified thickness is 10 mm and the specified depth is 5 mm.

In a fifth aspect combinable with any of the previous aspects, the control system is further configured to perform operations including controlling the load cell to remove the member from the mudcake sample by the force exerted on the member by the test apparatus.

In a sixth aspect combinable with any of the previous aspects, removing the member from the mudcake sample by the force exerted on the member by the test apparatus includes removing the member from the mudcake sample at a constant removal rate.

In a seventh aspect combinable with any of the previous aspects, removing the member from the mudcake sample by the force exerted on the member by the test apparatus includes removing the member from the mudcake sample in a linear direction.

In an eighth aspect combinable with any of the previous aspects, the control system is further configured to perform operations including maintaining, for a specified time duration, the member of the test apparatus in the mudcake sample prior to controlling the load cell to initiate removal of the member from the mudcake sample.

In a ninth aspect combinable with any of the previous aspects, the specified time duration includes 2 minutes.

In a tenth aspect combinable with any of the previous aspects, the exerted force includes a constant magnitude in a direction away from the mudcake sample.

In an eleventh aspect combinable with any of the previous aspects, the member includes a spherical member.

In a twelfth aspect combinable with any of the previous aspects, the mudcake preparation assembly includes a filter and a metallic screen.

In a thirteenth aspect combinable with any of the previous aspects, the mudcake preparation assembly includes an American Petroleum Institute (API) or a high pressure high temperature (HTHP) test apparatus.

In a fourteenth aspect combinable with any of the previous aspects, the mudcake preparation assembly is configured to filter the mudcake sample for a specified time duration.

In a fifteenth aspect combinable with any of the previous aspects, the specified time duration includes between one hour and 48 hours.

In a sixteenth aspect combinable with any of the previous aspects, the mudcake sample includes one of: a bentonite drilling fluid, a bentonite-salt drilling fluid, a potassium chloride polymer, or a low solids non-dispersed (LSND) drilling fluid.

In a seventeenth aspect combinable with any of the previous aspects, one or more properties of the mudcake sample include a sticking bond modulus (SBM) and an ultimate sticking bond strength (USBS).

In a eighteenth aspect combinable with any of the previous aspects, the control system is further configured to perform operations including graphically recording the force exerted on the member relative to the displacement distance.

In a nineteenth aspect combinable with any of the previous aspects, the control system is further configured to perform operations including determining at least one of the one or more properties based, at least in part, on the graphical recording of the force exerted on the member relative to the displacement distance.

In a twentieth aspect combinable with any of the previous aspects, the graphical recording of the force exerted on the member relative to the displacement distance includes a linear portion and a non-linear portion.

In a twenty-first aspect combinable with any of the previous aspects, the control system is further configured to perform operations including determining the SBM of the mudcake sample based on a slope of the non-linear portion of the graphical recording of the force exerted on the member relative to the displacement distance.

In a twenty-second aspect combinable with any of the previous aspects, the control system is further configured to perform operations including determining the USBS of the mudcake sample based on a peak exerted force value of the graphical recording of the force exerted on the member relative to the displacement distance.

In a twenty-third aspect combinable with any of the previous aspects, the control system is further configured to perform operations including recommending a drilling fluid for a drilling operation based, at least in part, on one or more of the determined properties.

In a twenty-fourth aspect combinable with any of the previous aspects, the control system is further configured to perform operations including recommending an additive for a drilling fluid for a drilling operation based, at least in part, on one or more of the determined properties.

In a twenty-fifth aspect combinable with any of the previous aspects, the control system is further configured to perform operations including determining an ease of recovery of a tubular member that is stuck in a wellbore based, at least in part, on one or more of the determined properties.

In a twenty-sixth aspect combinable with any of the previous aspects, the test apparatus is positioned at a wellsite location.

In another example implementation, a method includes (i) preparing a plurality of mudcake samples, each of the plurality of mudcake samples associated with a unique drilling fluid, each of the plurality of mudcake samples including a specified thickness; (ii) for each of the plurality of mudcake samples prepared in step (i): positioning a member of a test apparatus into the particular mudcake sample at a specified depth of the particular mudcake sample such that an interface between the member and the particular mudcake sample includes a contact area that is constant; removing the member from the mudcake sample by the force exerted on the member by the test apparatus, and recording, with the test apparatus, a force exerted on the member relative to a displacement distance of the member from the specified depth in the particular mudcake sample during removal of the member from the particular mudcake sample; and (iii) determining, with the test apparatus, one or more properties of each of the mudcake samples based on step (ii).

In a first aspect combinable with the example implementation, the specified thickness is at least 10 mm.

In a second aspect combinable with any of the previous aspects, the specified depth is half of the specified thickness.

In a third aspect combinable with any of the previous aspects, the specified thickness is 10 mm and the specified depth is 5 mm.

In a fourth aspect combinable with any of the previous aspects, removing the member from the particular mudcake sample by the force exerted on the member by the test apparatus includes removing the member from the particular mudcake sample at a constant removal rate.

In a fifth aspect combinable with any of the previous aspects, removing the member from the particular mudcake sample by the force exerted on the member by the test apparatus includes removing the member from the particular mudcake sample in a linear direction.

A sixth aspect combinable with any of the previous aspects further includes delaying, for a specified time duration, between positioning the member of the test apparatus into the particular mudcake sample and initiating removal of the member from the particular mudcake sample.

In a seventh aspect combinable with any of the previous aspects, the specified time duration includes 2 minutes.

In an eighth aspect combinable with any of the previous aspects, the member includes a spherical member.

In a ninth aspect combinable with any of the previous aspects, one or more properties of the mudcake sample include a sticking bond modulus (SBM) and an ultimate sticking bond strength (USBS).

In a tenth aspect combinable with any of the previous aspects, determining, with the test apparatus, one or more properties of each of the mudcake samples based on step (ii) includes determining at least one of the one or more properties based, at least in part, on a graphical recording of the force exerted on the member relative to the displacement distance.

An eleventh aspect combinable with any of the previous aspects further includes (iv) selecting a drilling mud based, at least in part, on the determined one or more properties.

Implementations of methods and systems for determining one or more properties associated with an adherence or sticking of a mudcake to a wellbore tubular member according to the present disclosure may include one or more of the following features. For example, such methods and systems may provide results to drilling engineers that provide guidance in drilling fluid, or drilling fluid additive, selection to reduce or eliminate stuck pipe. As another example, the results may provide guidance in recovering stuck pipe in a wellbore. As yet another example, methods and systems according to the present disclosure may provide a mudcake sticking potential measurement to evaluate mudcakes of different chemical compositions. The measurement may provide a predicted severity of a potential stuck pipe situation as well as predictive ease of recovering such stuck pipe. The measurement may include a predictive evaluation of a sticking bond strength (SBS) and ultimate SBS (USBS), as well as a sticking bond modulus (SBM), between a drill pipe and mudcake. Such predictive measurements may facilitate a proper selection of suitable drilling fluid ("mud") to create a low sticking mudcake on the wellbore wall, especially for a high permeable subterranean zone. As another example, such methods and systems may minimize or help minimize a scope of differential sticking. The reduction of monetary loss due to pipe sticking or pipe lost in the wellbore may also be achieved. Further, undesirable expenses related to lost drilling time due to stuck pipe may be minimized by, for instance, proper selection of drilling fluid based on the measurement results. As another example, drilling hazards may be reduced significantly by potentially mitigating the scope of pipe sticking problems, especially differential sticking problems in highly permeable sticking prone zones.

This disclosure also describes implementations of methods and systems for determining one or more properties of a spotting fluid for reducing an adherence or sticking of a mudcake to a wellbore tubular member. In a general implementation, a method includes positioning a member of a test apparatus into a prepared mudcake sample at a specified depth of the mudcake sample, the mudcake sample associated with a drilling fluid and including a specified thickness; circulating a flow of a spotting fluid to contact the prepared mudcake sample in a test cell of the test apparatus; soaking the prepared mudcake sample in the spotting fluid for a specified time duration; subsequent to the specified time duration, detecting, with the test apparatus, a force exerted on the member relative to a displacement distance of the member from the specified depth in the mudcake sample during removal of the member from the mudcake sample; recording, with the test apparatus, the detected force relative to the displacement distance; and determining, with the test apparatus, one or more properties associated with the mudcake sample based on the recorded force relative to the displacement distance.

An aspect combinable with the general implementation further includes collecting an overflow of the spotting fluid that flows from the test cell.

In another aspect combinable with any of the previous aspects, circulating the flow of the spotting fluid includes circulating, by a gravity feed, the spotting fluid from a feeder tank to the test cell.

In another aspect combinable with any of the previous aspects, the feeder tank is positioned vertically above the test cell.

In another aspect combinable with any of the previous aspects, circulating the flow of the spotting fluid includes circulating a pressurized flow of the spotting fluid from a feeder tank to the test cell.

Another aspect combinable with any of the previous aspects further includes pressurizing the spotting fluid in the feeder tank with a pressurized gas stored in a gas tank in fluid communication with the feeder tank.

Another aspect combinable with any of the previous aspects further includes regulating a pressure of the pressurized gas circulating from the gas tank to the feeder tank.

Another aspect combinable with any of the previous aspects further includes initiating removal of the member from the mudcake sample by the force exerted on the member by the test apparatus.

In another aspect combinable with any of the previous aspects, the specified thickness is 10 mm and the specified depth is 5 mm.

Another aspect combinable with any of the previous aspects further includes removing the member from the mudcake sample by the force exerted on the member by the test apparatus.

In another aspect combinable with any of the previous aspects, removing the member from the mudcake sample by the force exerted on the member by the test apparatus includes removing the member from the mudcake sample at a constant removal rate.

Another aspect combinable with any of the previous aspects further includes maintaining, for a specified time period, the member in the mudcake sample prior to circulating the spotting fluid.

In another aspect combinable with any of the previous aspects, the specified time period includes 2 minutes.

In another aspect combinable with any of the previous aspects, the member includes a spherical member.

In another aspect combinable with any of the previous aspects, one or more properties of the mudcake sample include a sticking bond modulus (SBM) and an ultimate sticking bond strength (USBS).

Another aspect combinable with any of the previous aspects further includes determining at least one of the one or more properties based, at least in part, on the graphical recording of the force exerted on the member relative to the displacement distance.

Another aspect combinable with any of the previous aspects further includes performing an action based at least in part on the one or more of the determined properties.

In another aspect combinable with any of the previous aspects, the action includes at least one of selecting a drilling fluid to use in a drilling operation; selecting a particular spotting fluid to use in a stuck-pipe removal operation; or determining an ease of recovery of a tubular member that is stuck in a wellbore.

In another general implementation, a spotting fluid testing system includes a test apparatus and a control system communicably coupled to the test apparatus. The test apparatus includes mudcake holder configured to restrain a mudcake sample in a stationary position; a load cell; and a testing member coupled to the load cell. The control system is configured to perform operations including: controlling the load cell to position the member into the mudcake sample at a specified depth of the mudcake sample; controlling one or more valves of the test apparatus to circulate a flow of a spotting fluid to contact and soak the mudcake sample in a test container of the test apparatus; subsequent to a specified soaking time duration, controlling the load cell to initiate removal of the member from the mudcake sample by a force exerted on the member by the load cell; detecting, with the test apparatus, a force exerted on the member relative to a displacement distance of the member from the specified depth in the mudcake sample during removal of the member from the mudcake sample; recording, with the test apparatus, the detected force relative to the displacement distance; and determining one or more properties of the mudcake sample based on the recorded force relative to the displacement distance.

An aspect combinable with the general implementation further includes a collection tank fluidly coupled to the test cell.

In another aspect combinable with any of the previous aspects, the control system is further configured to perform operations including controlling one or more valves of the test apparatus to circulate an overflow of the spotting fluid from the test cell to the collection tank.

Another aspect combinable with any of the previous aspects further includes a feeder tank positioned vertically above the test cell to circulate the flow of the spotting fluid from the feeder tank to the test cell by a gravity feed.

Another aspect combinable with any of the previous aspects further includes a gas tank that stores a pressurized gas, the gas tank fluidly coupled with the feeder tank.

In another aspect combinable with any of the previous aspects, is the control system further configured to perform operations including controlling one or more valves to circulate the pressurized gas to the feeder tank to generate a pressurized flow of the spotting fluid from the feeder tank to the test cell.

In another aspect combinable with any of the previous aspects, the control system is further configured to perform operations including controlling a pressure regulator of the gas tank to adjust a pressure of the pressurized gas circulating from the gas tank to the feeder tank.

In another aspect combinable with any of the previous aspects, the control system is further configured to perform operations including initiating removal of the member from the mudcake sample by the force exerted on the member by the test apparatus.

In another aspect combinable with any of the previous aspects, the specified thickness is 10 mm and the specified depth is 5 mm.

In another aspect combinable with any of the previous aspects, the control system is further configured to perform operations including removing the member from the mudcake sample by the force exerted on the member by the test apparatus.

In another aspect combinable with any of the previous aspects, removing the member from the mudcake sample by the force exerted on the member by the test apparatus includes removing the member from the mudcake sample at a constant removal rate.

In another aspect combinable with any of the previous aspects, the member includes a spherical member.

In another aspect combinable with any of the previous aspects, one or more properties of the mudcake sample include a sticking bond modulus (SBM) and an ultimate sticking bond strength (USBS).

In another aspect combinable with any of the previous aspects, the control system is further configured to perform operations including determining at least one of the one or more properties based, at least in part, on the graphical recording of the force exerted on the member relative to the displacement distance.

In another aspect combinable with any of the previous aspects, the control system is further configured to perform operations including recommending an action based at least in part on the one or more of the determined properties.

In another aspect combinable with any of the previous aspects, the action includes at least one of: selecting a drilling fluid to use in a drilling operation; selecting a particular spotting fluid to use in a stuck-pipe removal operation; or determining an ease of recovery of a tubular member that is stuck in a wellbore.

Implementations of methods and systems for determining one or more properties associated with a spotting fluid for reducing an adherence or sticking of a mudcake to a wellbore tubular member according to the present disclosure may include one or more of the following features. For example, such methods and systems may provide results to drilling engineers that provide guidance in selecting a spotting fluid or spotting fluid composition to use to recover a tubular member stuck in a wellbore. As another example, methods and systems according to the present disclosure may provide a mudcake sticking potential measurement to evaluate spotting fluids of different chemical compositions. The measurement may provide a predicted severity of a potential stuck pipe situation as well as predictive ease of recovering such stuck pipe through application, in the wellbore, of the particular spotting fluid. The measurement may include a predictive evaluation of a sticking bond strength (SBS) and ultimate SBS (USBS), as well as a sticking bond modulus (SBM), between a drill pipe and mudcake when a particular spotting fluid is used. Such predictive measurements may also facilitate a proper selection of suitable drilling fluid ("mud") to create a low sticking mudcake on the wellbore wall, especially for a high permeable subterranean zone. As another example, such methods and systems may minimize or help minimize a scope of differential sticking. The reduction of monetary loss due to pipe sticking or pipe lost in the wellbore may also be achieved. Further, undesirable expenses related to lost drilling time due to stuck pipe may be minimized by, for instance, proper selection of drilling fluid based on the measurement results. As another example, drilling hazards may be reduced significantly by potentially mitigating the scope of pipe sticking problems, especially differential sticking problems in highly permeable sticking prone zones. As an even further example, prevention of pipe sticking through the use of an appropriately selected spotting fluid may reduce other drilling problems associated with pipe sticking, and thus can lead to a significant reduction in non-productive time (NPT).

The details of one or more implementations of the subject matter described in this disclosure are set forth in the accompanying drawings and the description herein. Other features, aspects, and advantages of the subject matter will become apparent from the description, the drawings, and the claims.

BRIEF DESCRIPTION OF THE DRAWINGS

FIGS. 5A-5D are graphical representations that illustrate a pulling force relative to upward displacement during testing of mudcake samples of specific compositions.

DETAILED DESCRIPTION

Figure 1:
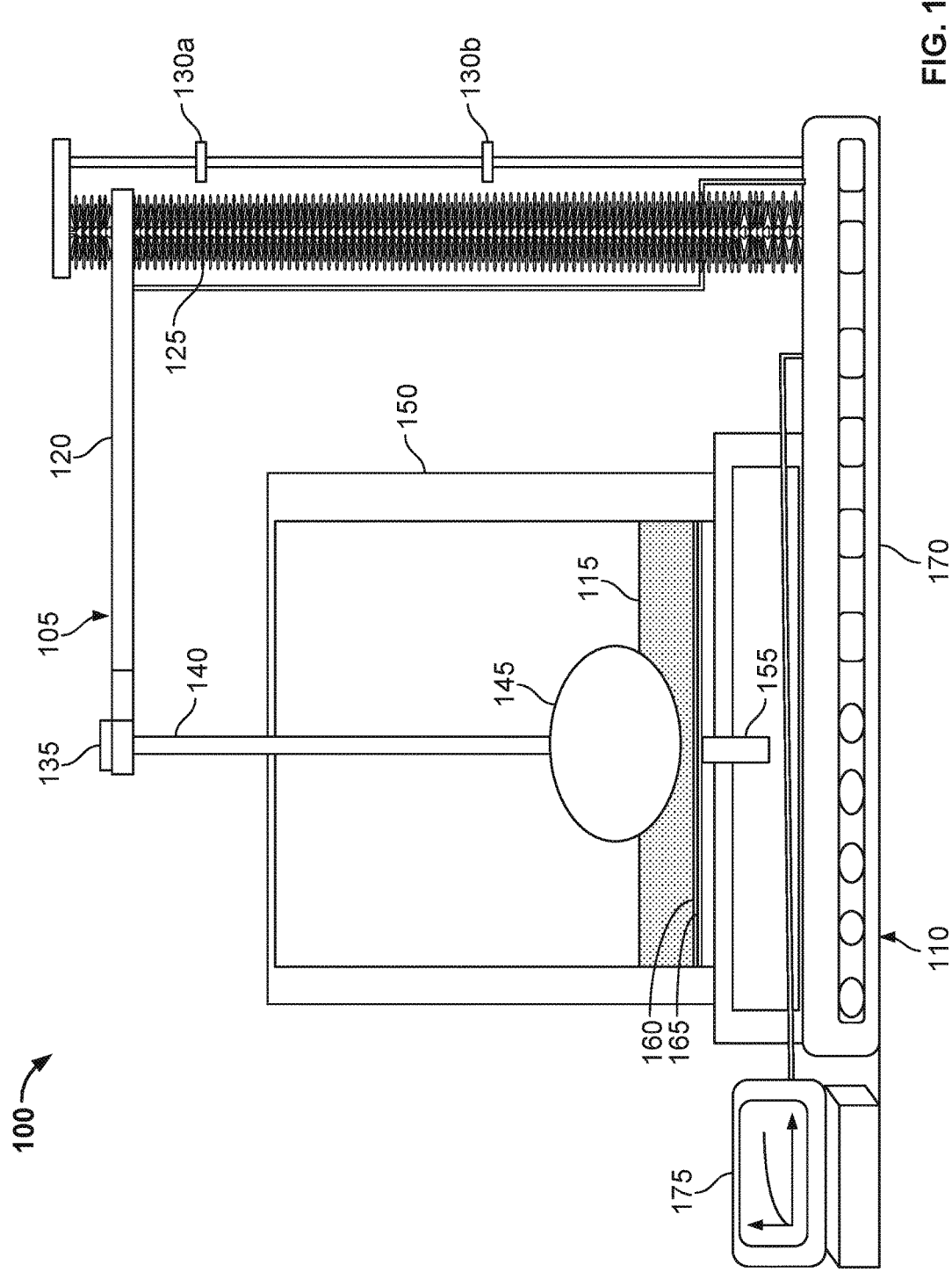
FIG. 1 is a schematic diagram of an implementation of a mudcake testing system.

FIG. 1 is a schematic diagram of an implementation of a mudcake testing system 100. The mudcake testing system 100 is used to test or validate a theoretical response of removing (for example, unsticking) of an object imbedded in a prepared mudcake sample. Thus, the system 100 may be used to test or validate a theoretical response to unsticking a portion of a wellbore tubular (for example, drill pipe or a portion of a drilling assembly) that is embedded in a mudcake of a wellbore. A mudcake sample 115, illustrated in FIG. 1, represents a portion of a mudcake in a wellbore that is developed during drilling or other wellbore operations. Generally, the mudcake sample 115 represents residue deposited on a permeable medium (for example, a wellbore wall) that develops when drilling fluid is deposited against the wellbore wall under pressure. Because liquid is able to pass through the permeable medium, a sticky substance, called a "mudcake," may be left to form on the wellbore wall. The mudcake has certain properties based on, for instance, the drilling fluid used in the drilling operation. Such properties relate to the thickness (for example, which affects hydrocarbon production), toughness, slickness (for example, which affects an affinity to adhere or not to tubular drilling components), and permeability (for example, also affecting production). Mudcakes that form on permeable zones in the wellbore can cause stuck pipe and other drilling problems. Thus, the testing system 100 can be used to determine one or more properties of the mudcake sample 115, which is used to predict a stuck pipe situation, other problems. The properties may also be used to select drilling fluids, drilling fluid additives, and otherwise.

The illustrated implementation of the mudcake testing system 100 includes a load cell 105 that is communicably coupled to a control system 110. Several example load cells may be used as the load cell 105, including, without limitation, a uniaxial load cell, a triaxial load cell, a biaxial load cell, a strain-gauge load cell, a hydraulic load cell, or a pneumatic load cell. In some aspects, the load cell 105 is capable of applying 50 kilograms-force (kgf) or less of force in operation of the system 100.

The load cell 105 includes carrier arm 120 mounted on a load stand 125. The load stand 125 operates to lower and raise the carrier arm 120, and by extension a testing member 145 mounted on a test leg 140 coupled to the carrier arm 120, with a variable mount of force. As illustrated in this implementation, an upper position limiter 130a and a lower position limiter 130b is mounted adjacent the load stand 125 to provide upper and lower movement limits of the carrier arm 120 during operation of the mudcake testing system 100.

The mudcake testing system 100 also includes a test cell 150. The test cell 150 can be an API test cell according to (for example, an API test cell or high temperature-high pressure (HTHP) test cell) into which a prepared mudcake sample 115 is placed. Example test cells can include: a Faring Instrument No. 101502980 or No. 101533370; an OFI Testing Equipment, Inc. 140-40 Water Loss Press 4 Unit, serial #14-15; or an OFI Testing Equipment, Inc. 170-00 OFITE HTHP Press, Single End Test Cell.

In this implementation, the mudcake sample 115 is placed on top of a filter 160, which in turn is placed on top of a screen 165 (for example, metallic screen). The illustrated test cell 150 includes an outlet 155 positioned at a bottom, for example, to allow liquid to drain from the mudcake sample 115 if necessary.

The illustrated control system 110, in this implementation, comprises a processor based controller 170 (for example, CPU) that is communicably coupled to a data logger 175. The controller 170 includes an input peripheral (for example, keyboard, toggles, button, mouse, or otherwise) for use by an operator (for example, to input operational constraints) as well as an output peripheral. The controller 170 is coupled with the load cell 105 (for example, through one or more wires or wirelessly) to receive data output from the load cell 105 during operation of the mudcake testing system 100. For example, data such as force applied by the load stand 125 (for example, upward) on the member 145 (for example, through the carrier arm 120 and the leg 140), as well as position of the member 145 (for example, initial position in contact in the mudcake sample 115, relative distance of the member 145 from an initial position, or both), may be transmitted to or received by the controller 170.

The implementation of the load cell 105 includes a calibration platform 135. The calibration platform 135 receives a signal from the load cell 105 that represents the force applied on the test member 145 during operation of the testing system 100. The calibration platform 135 then calculates a relationship between the detected signal and the force. For example, the load cell 105 detects and measures an electrical resistance signal that is proportional to the force applied to the test member 145. The electrical resistance signal is then converted to a force signal to be output by the control system 110.

The data logger 175 includes an output device for display of the data (for example, force, displacement distance, or other data) sent to the controller 170 from the load cell 105. Example outputs include graphical representations of force versus displacement curves are shown for various mudcake samples 115 in FIGS. 5A-5D.

Figure 2:
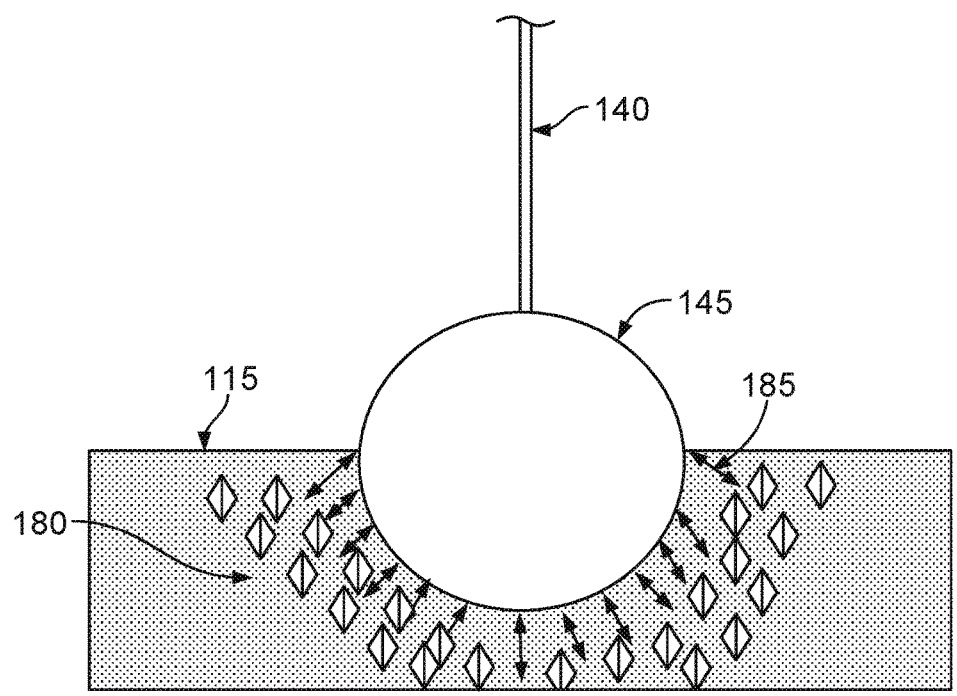
FIG. 2 is a schematic diagram of a portion of an implementation of a mudcake testing system.

FIG. 2 is a schematic diagram of a portion of an implementation of the mudcake testing system 100. More specifically, FIG. 2 illustrates an interface between the member 145 and the mudcake sample 115, including bonds that develop once the member 145 is inserted into the mudcake sample 115 that is positioned in the test cell 150. Generally, once an object, such as the member 145 that represents a wellbore tubular, is embedded into a matrix of a mudcake (for example, the mudcake sample 115), adhesive bonds develop between the object and the mudcake interface due to the alteration of free surface energy at the contacting surfaces of the mudcake sample 115 and the embedded object (for example, the member 145). The sticking bonds are the combined results of adhesive and cohesive bonds and are governed by the resultant effect of interfacial tension, Vander der Waal forces, inter-atomic and inter-molecular forces, hydrogen and ionic bonds, and otherwise.

As the magnitude of these forces varies depending on the composition of the mudcake sample 115, physics and chemistry of the drilling fluid and drilling fluid additives and also the physics and chemistry of the base fluid used in preparing the drilling fluid, mudcakes deposited by various drilling systems have significantly different sticking bond characteristics. Such characteristics are sticking bond modulus (SBM) (for example, a rate of increase of a pull resistance of a mudcake) and ultimate sticking bond strength (USBS). The higher the strength of the surface tension, molecular and atomic forces, strength of ionic and hydrogen bondings, the stronger the sticking bonds between the member 145-mudcake sample 115 interface. As the sticking bonds are stronger, a higher pulling force (for example, by the load stand 125) is required to unstick the member 145 from the mudcake sample 115. Likewise, in wellbore operations, as the sticking bonds between a wellbore mudcake and wellbore tubular become stronger, a higher pulling force (for example, by a drill string) is required to unstick the wellbore tubular from the wellbore mudcake.

As shown, the member 145 embedded into mudcake sample 115 experiences interfacial adhesive bonds 185 and cohesive matrix bonds 180 that adhere the member 145 with the mudcake sample 115. If such adhesive bonds 185 and cohesive bonds 180 are weak, then the member 145 is released more easily based on an upward force applied to the member 145 from the load stand 125 (for example, pulling the member 145 out of the sample 115). On the other hand, a mudcake sample 115 that creates strong adhesive bonds 185 and cohesive bonds 180 at the mudcake-member interface may require a higher upward pull (for example, by the load stand 125) to release from the mudcake sample 115.

As illustrated in the implementation of the mudcake testing system 100 shown in FIGS. 1 and 2, the member 145 comprises a spherically-shaped member. Other implementations of a mudcake testing system according to the present disclosure may include alternatively-shaped members, such as cylindrical, egg-shaped, or otherwise. In some aspects, the spherical member 145 is used to more accurately determine one or more properties (for example, SBM, USBS, or otherwise) of the mudcake sample 115 as compared to, for example, a tubular or cylindrically-shaped member. For instance, even though a wellbore component that sticks to a wellbore mudcake is typically cylindrical in cross section (for example, drill pipe, a drill string, or other tubular component), use of a cylindrical member may not provide accurate readings due to the sharp edges that would be present on a cylindrical member. In short, the spherical member 145, in some aspects, may better represent a wellbore tubular for more accurate determination of the mudcake properties.

Figure 3:
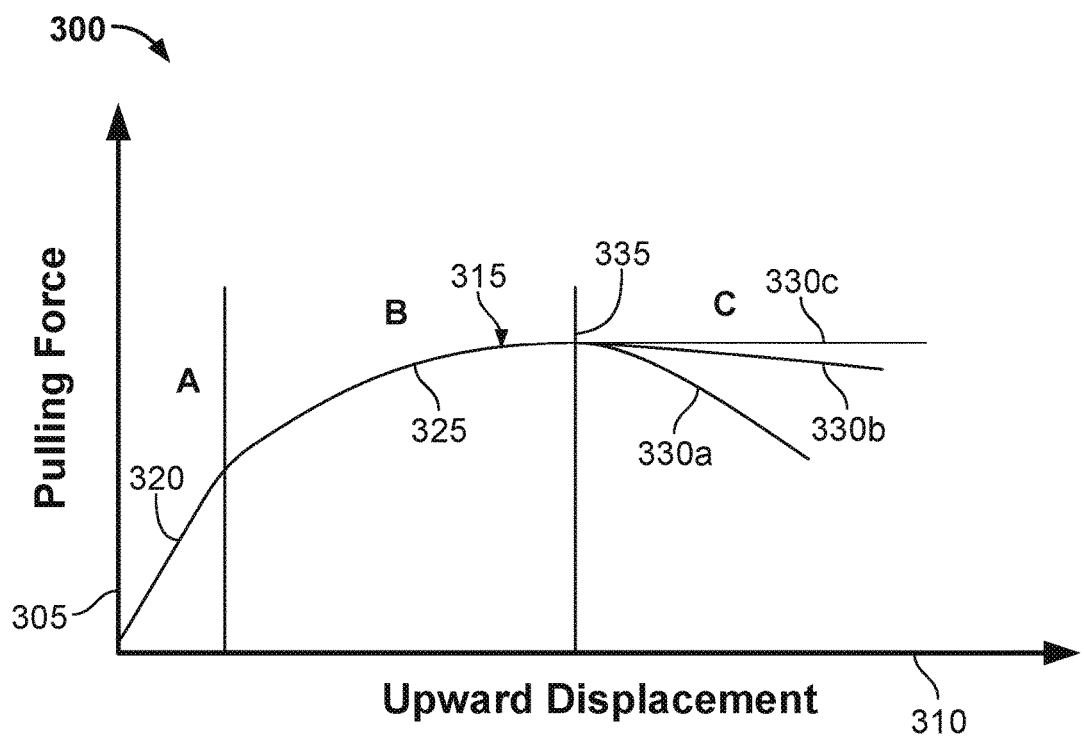
FIG. 3 is a graphical representation that illustrates a pulling force relative to upward displacement during testing of a mudcake sample.

FIG. 3 is a graphical representation 300 that illustrates a pulling force relative to upward displacement during testing of a mudcake sample. Generally, the graphical representation 300 represents a hypothetical force versus displacement curve that is generated during operation of a mudcake testing system, such as system 100. As illustrated, the graphical representation 300 includes a y-axis 305 that represents a pulling force and an x-axis 310 that represents an upward displacement. For instance, the upward displacement is a distance (for example, a linear distance) from an initial placement of a member of the testing system (for example, embedded in a mudcake sample) at a particular magnitude of force applied (for example, upwardly) to the member.

As shown, a force-displacement curve 315 is generated, which includes a linear portion 320 and a non-linear portion 325. The linear portion 320 represents elastic extension of the sticking bonds under the action of the pulling force. In some aspects, a slope of the linear portion 320 represents a magnitude of the sticking bond modulus (SBM) and is a characteristics parameter of the sticking bonds. Different mudcake compositions and their respective sticking bond toughness, therefore, may be compared using the SBM.

The non-linear portion 325 of the curve 315 that represents progressive damage and degradation of the sticking bonds until a peak value 335 is reached. The peak value 335 of the pulling force is defined as the ultimate sticking bond strength (USBS). Different mudcake compositions and their respective sticking bond strength, therefore, may be compared using the USBS.

The initiation of damage or failure of weak sticking bonds, and the rearrangement and reorientation of particles of the existing bonds at the end of the elastic extension limit (for example, the linear portion 320) causes progressive damage of the bonds and thus the continuous flattening of the curve 315. The non-linear portion 325 includes an intermediate portion (labeled B) from the linear portion 320 to the peak value 335 of the sticking bonds. In some real-world instances of force versus displacement curves (for example, as shown in FIGS. 5A-5D), the peak value, that is, the USBS, may not be well defined in the curve 315 due to the deformation hardening or constant load deformation effect that may linger. For example, as shown, extension of the non-linear portion 325 into one of paths 330a-330c indicates deformation softening, constant load deformation, or deformation hardening, respectively.

Figure 4:
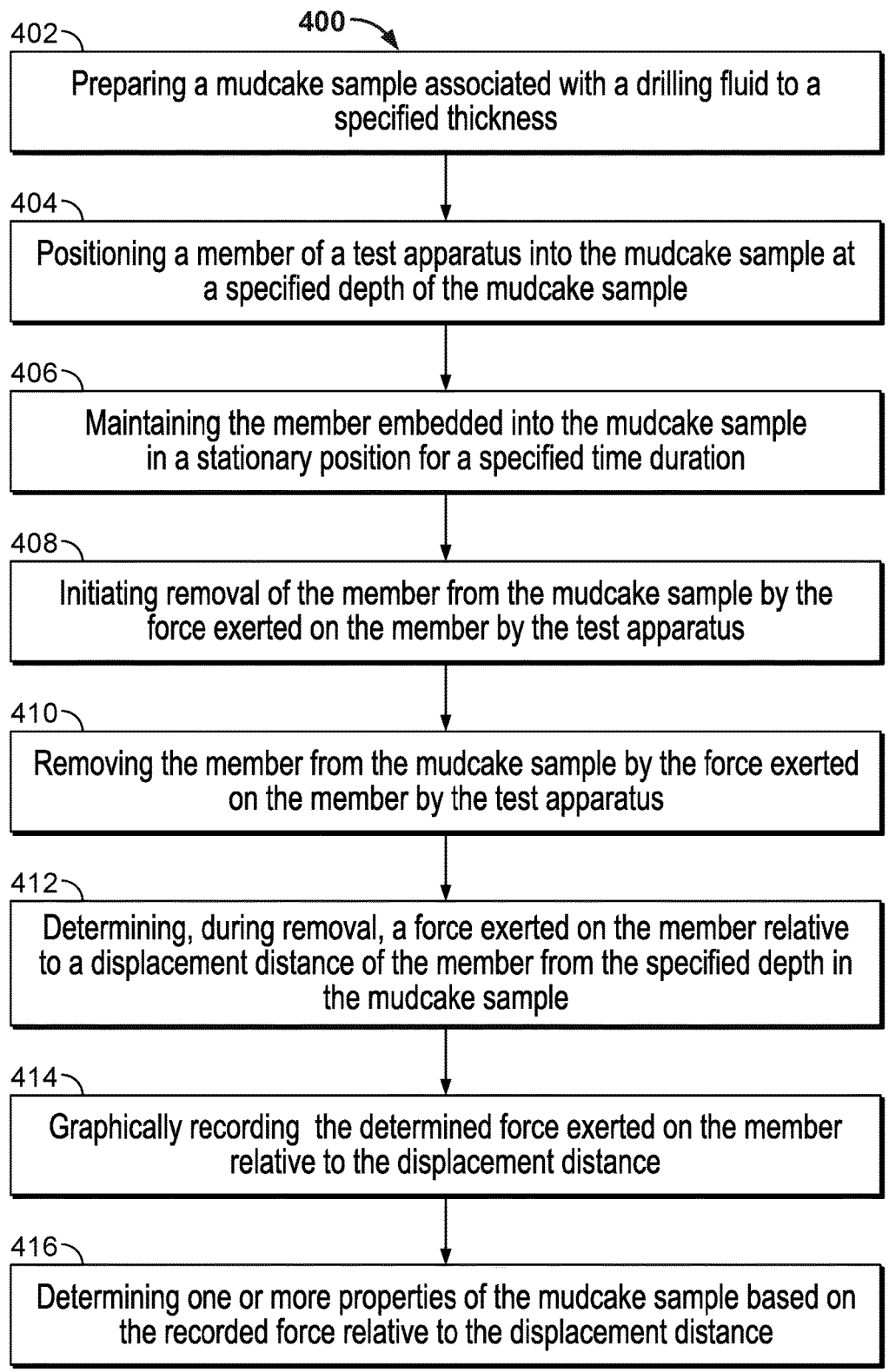
FIG. 4 is a flowchart that describes an example method for testing a mudcake sample.

FIG. 4 is a flowchart that describes an example method for testing a mudcake sample. In some aspects, method 400 may be implemented by the mudcake testing system 100 or other mudcake testing systems according to the present disclosure, either at a wellsite location or off site from well operations.

Method 400 may begin at step 402, which includes preparing a mudcake sample associated with a drilling fluid to a specified thickness. In some aspects, preparation of mudcake sample with sufficient mudcake thickness may improve the accuracy and reliability of mudcake sticking properties to be determined through method 400. For example, in some aspects, a mudcake sample is prepared so that the thickness is at least 10 mm, which may reduce or eliminate a base effect that creates inaccuracies in the test results. For example, the base effect occurs when adhesion of the mudcake sample to a base on which it is supported effects the sticking properties of the mudcake sample to a test member (for example, member 145). The base effect, therefore, renders test results inaccurate if the mudcake is prepared too thinly to minimize the effect.

In this implementation of method 400, the mudcake sample may be prepared using an API test cell as described previously. As part of the preparation step, in some implementations, a filtration step is included. Conventionally, filtration time for mudcake preparation is about 30 minutes as defined in the API fluid loss test, API RP 10B-2 Static Fluid Loss Test, Section 10 ($2^{nd}$ ed., April 2013). In implementations of method 400, however, the filtration time was varied between an hour and 48 hours (roughly). Water-based mud testing procedures are in accord with API RP 13-B1, $3^{rd}$ ed., 2003, while oil-based mud testing procedures are in accord with API RP 13-B2, $3^{rd}$ ed., 1998.

Of course, the present disclosure also contemplates that a mudcake sample prepared to be analyzed with subsequent steps of method 400 may be prepared by a third party. Thus, a third party may prepare a mudcake sample while a testing party may receive (for example, purchase) the prepared mudcake from the third party for subsequent testing.

Step 402, in four specific examples, can be used to prepare mudcake samples of different compositions with different filtration times. For example, Table 1 shows the four specific examples prepared using step 402:

TABLE 1

| Type of mud | Filtration Duration to Produce Mudcake | Criteria for Filtration Time |
| --- | --- | --- |
| Bentonite | 24 hours (hrs) | Produce mudcake with a thickness of > 10 mm |
| Bentonite + salt | 2 hrs | |
| Potassium Chloride (KCl)-Polymer | 48 hrs | |
| LSND | 48 hrs | |

As noted in Table 1, salt water bentonite (sodium chloride (NaCl) plus bentonite) mud took a short time to produce a mudcake of 10 mm or more thickness. Bentonite, LSND, KCl-Polymer muds took much longer time to produce a mudcake of 10 mm or more thickness. The compositions of these four example mudcake samples are shown in Table 2 (where "cc" is cubic centimeters and "ppb" is pounds per barrel):

TABLE 2

| Material | Bentonite Mud | NaCl-Bentonite Mud | KCl-Polymer Mud | LSND Mud |
| --- | --- | --- | --- | --- |
| Water (cc) | 350 | 350 | 274.4 | 268.1 |
| Bentonite (ppb) | 20 | 20 | — | — |
| NaCl (ppb) | — | 25 | — | 48 |
| NaOH/KOH (ppb) | | | 0.25 | 0.25 |
| Starch (ppb) | | | 5 | 4 |

TABLE 2-continued

| Material | Bentonite Mud | NaCl-Bentonite Mud | KCl-Polymer Mud | LSND Mud |
|---|---|---|---|---|
| XC Polymer (ppb) | | | 0.875 | 0.625 |
| PAC-L (ppb) | | | 0.75 | — |
| KCl (ppb) | | | 37 | — |
| Lime (ppb) | | | 0.25 | — |
| Rev Dust (ppb) | 25 | 25 | — | — |
| Sodium Sulfite (ppb) | | | 0.25 | — |
| Soltex (ppb) | | | 3 | — |
| CaCO$_3$-fine (ppb) | | | — | 130 |
| CaCO$_3$-medium (ppb) | | | 20 | 11 |
| Barite (ppb) | | | 257 | — |

With reference to Table 2, XC polymer is a xanthun gum polymer, PAC-L is a low viscosity polyanionic cellulose, Rev Dust are clay particles used to simulate drill solids, CaCO$_3$-fine is calcium carbonate at D50 size 10-14 microns, and CaCO$_3$-medium is calcium carbonate at D50 size 135-165 microns.

Subsequent to mudcake sample preparation in step 402, the sample may be gently washed to remove top loose material (for example, with water to avoid damage to the sample) and placed in a test system. The test system includes a test cell such as test cell 150. In the test cell, the mudcake sample is positioned so that a member of the test system, when brought in contact with the mudcake sample, contacts roughly a center location of the sample.

Method 400 may continue at step 404, which includes positioning a member of a test apparatus into the mudcake sample at a specified depth. For example, in some implementations, the member is pushed into the mudcake sample to a depth equal or about equal to 50% of the thickness of the prepared mudcake sample. For example, with a mudcake sample of about 10 mm, the depth would be about 5 mm. Once embedded in the mudcake sample, the previously-described sticking bonds form between the member and the mudcake sample.

In some aspects, by preparing the mudcake sample prior to positioning the member into the sample (for example, by not preparing the sample around the member to begin with), a shielding effect on the testing member may be avoided to increase test accuracy. For example, conventionally, mudcake sample testing occurs by preparing a mudcake sample so it forms around a testing member that is already in place. The shielding effect of the test member includes a mechanical barrier that is created during the deposition of mudcake particles as the mudcake sample is formed while the testing member is present in the filtration cell of the testing system. In the conventional techniques, the mudcake sample is thinner at a bottom of the member but thicker outside the domain of the member. Hence, the mudcake sample creates more contact at the edges of the mudcake-member interface but fewer contacts at the bottom of the mudcake sample.

The presence of the testing member before the start of deposition of mudcake particles is a mechanical barrier for some particles and thus hamper the formation of the mudcake sample below the testing member (for example, between the member and a filter, such as filter 160). Further, the shielding effect may prevent the mudcake test from most accurately representing a real-world situation in which a wellbore tubular becomes stuck to a mudcake in a wellbore. For example, during a stuck pipe situation, intimate and higher numbers of bondings or contacts are formed at the center of pipe-mudcake interface. Thus, by first forming the mudcake sample outside of the presence of the member, the shielding effect is minimized and a real-world situation may be better replicated.

Method 400 may continue at step 406, which includes maintaining the test member embedded into the mudcake sample in a stationary position for a specified time duration. For example, in order to ensure that the sticking bonds have fully formed, the member may sit embedded in the mudcake sample for two minutes or more. This specified time duration, which may depend, for instance, on mudcake composition, mudcake thickness, and other criteria, allows the adjustment and stabilization of the sticking bonds that link the testing member and the mudcake sample.

Method 400 may continue at step 408, which includes initiating removal of the member from the mudcake sample by a force exerted on the member by the testing system (for example, by a load cell). By initiating removal, the member is pulled upward in a linear motion (for example, without or with negligible rotation) at a particular force and rate. For example, the load cell exerts a force on the member to initiate removal at about 0.5 mm/min removal rate.

Method 400 may continue at step 410, which includes removing the member from the mudcake sample by the force exerted on the member by the testing system. In this example, implementation, the member is pulled, linearly, out of the mudcake sample until it is free from the sample. The pull rate may remain constant or substantially constant (for example, within ±1-5% difference) in steps 408 and 410.

In some implementations, an initial contact area of an interface between the mudcake sample and member is established in step 404, when the member is positioned into the mudcake sample, thereby establishing contact (and the sticking bonds) between the member and the mudcake sample. In some aspects, as steps 408 and 410 are implemented for multiple mudcake samples, the initial contact area between the mudcake sample and the testing member remains substantially constant (for example, within ±1-5% difference) for each mudcake sample that is tested. By forming the mudcake sample with a particular thickness outside of the presence of the member (as explained previously), different mudcake sample compositions are more accurately compared by having each different mudcake sample have a similar and constant initial contact area with the testing member. For example, mudcake sample testing based on an initial constant contact area may provide for more accurate comparative evaluation of the mechanical characteristics and sticking properties of water and oil-based muds used in drilling operations.

Method 400 may continue at step 412, which includes determining, during removal, a force exerted on the member relative to a displacement distance of the member from the specified depth in the mudcake sample. For example, a signal representative of the force exerted on the member, such as an electrical resistance signal, is detected by the load cell. The load cell then transforms the electrical resistance signal to a force value.

Method 400 may continue at step 414, which includes graphically recording the determined force exerted on the member relative to the displacement distance. For example, as the member is upwardly moved away from the mudcake sample (for example, at a constant or substantially constant rate), the sticking bonds between the mudcake sample and the testing member exerts a pulling force in a downward direction. This pulling force is measured, for example, by a control system as part of testing system. The control system, as shown in the example of FIG. 1, is communicably coupled to the load cell to receive force and displacement measurements. As the member is forcibly displaced from an initial position (for example, embedded in the mudcake sample), force versus distance is recorded.

Continuing with the four specific mudcake samples described previously, FIGS. 5A-5D are graphical representations 500, 520, 540, and 560, respectively, of triplicate tests in which step 414 is implemented to graphically record the determined force versus displacement distance. Each of FIGS. 5A-5D show the pulling force versus upward displacement curves of the water-based mudcakes described previously.

Figure 5A:
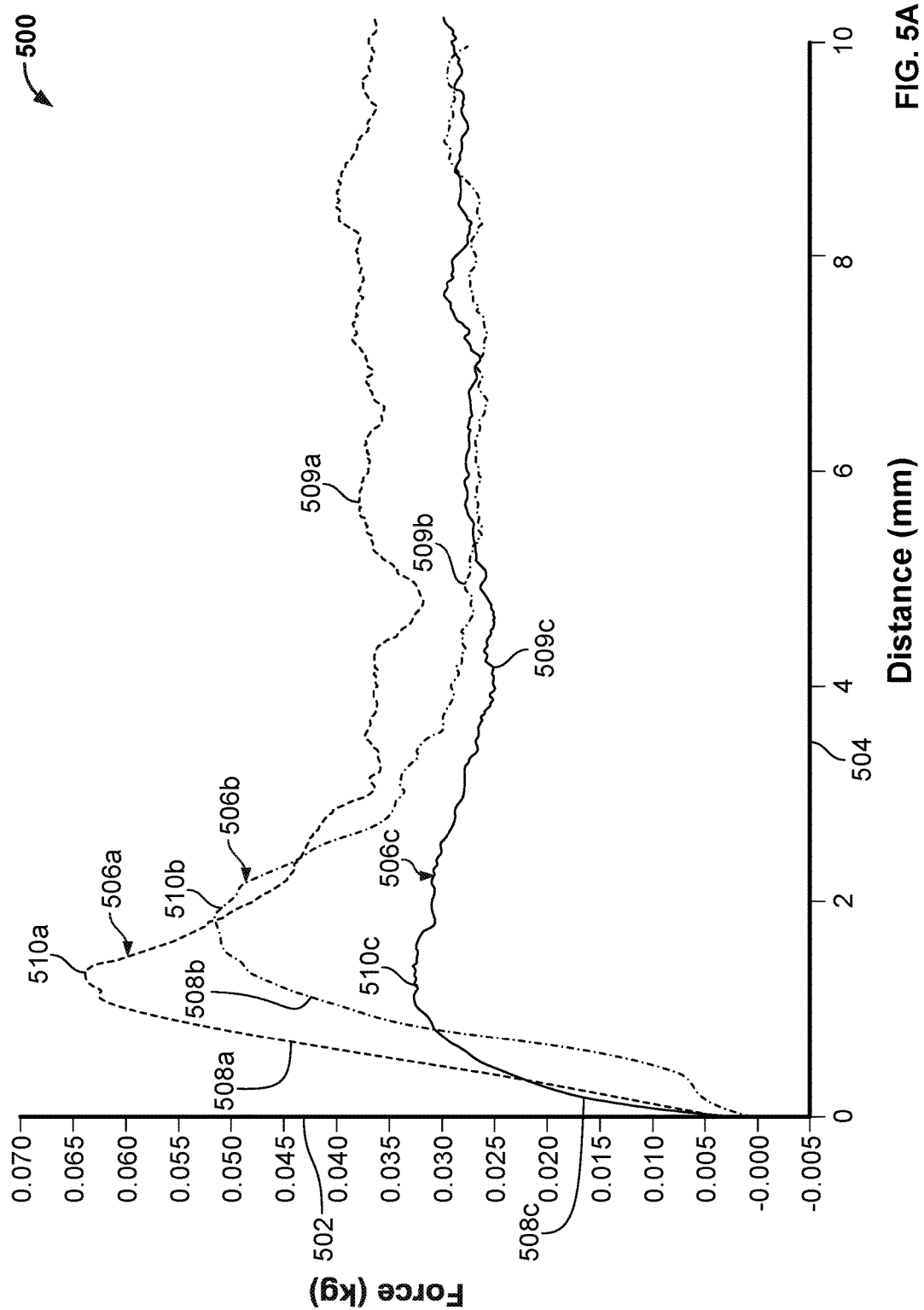

FIG. 5A shows the triplicate tests for the bentonite mudcake and includes a y-axis 502 which represents force in kilograms, an x-axis 504 that represents distance in millimeters. Curves 506a-506c show the result of three independent implementations of method 400, including step 414. Each curve 506a-506c includes a respective linear portion 508a-508c, a respective non-linear portion 509a-509c, and a respective peak 510a-510c. As described previously, a slope of a linear portion of the curves 506a-506c represents or approximates the SBM of the particular mudcake sample. The peak of the curves 506a-506c represents or approximates the USBS of the particular mudcake sample. In this example, mean values were determined from the curves 506a-506c to determine an average SBM in kilograms-force per millimeter (kgf/mm) and USBS in kilograms-force (kgf) for the bentonite mudcake sample.

FIG. 5B shows the triplicate tests for the salt water bentonite mudcake and includes a y-axis 522 which represents force in kilograms, an x-axis 524 that represents distance in millimeters. Curves 526a-526c show the result of three independent implementations of method 400, including step 414. Each curve 526a-526c includes a respective linear portion 528a-528c, a respective non-linear portion 529a-529c, and a respective peak 530a-530c. A slope of a linear portion of the curves 526a-526c represents or approximates the SBM of the particular mudcake sample. The peak of the curves 526a-526c represents or approximates the USBS of the particular mudcake sample. In this implementation, mean values were determined from the curves 526a-526c to determine an average SBM (kgf/mm) and USBS (kgf) for the salt water bentonite mudcake sample.

Figure 5C:
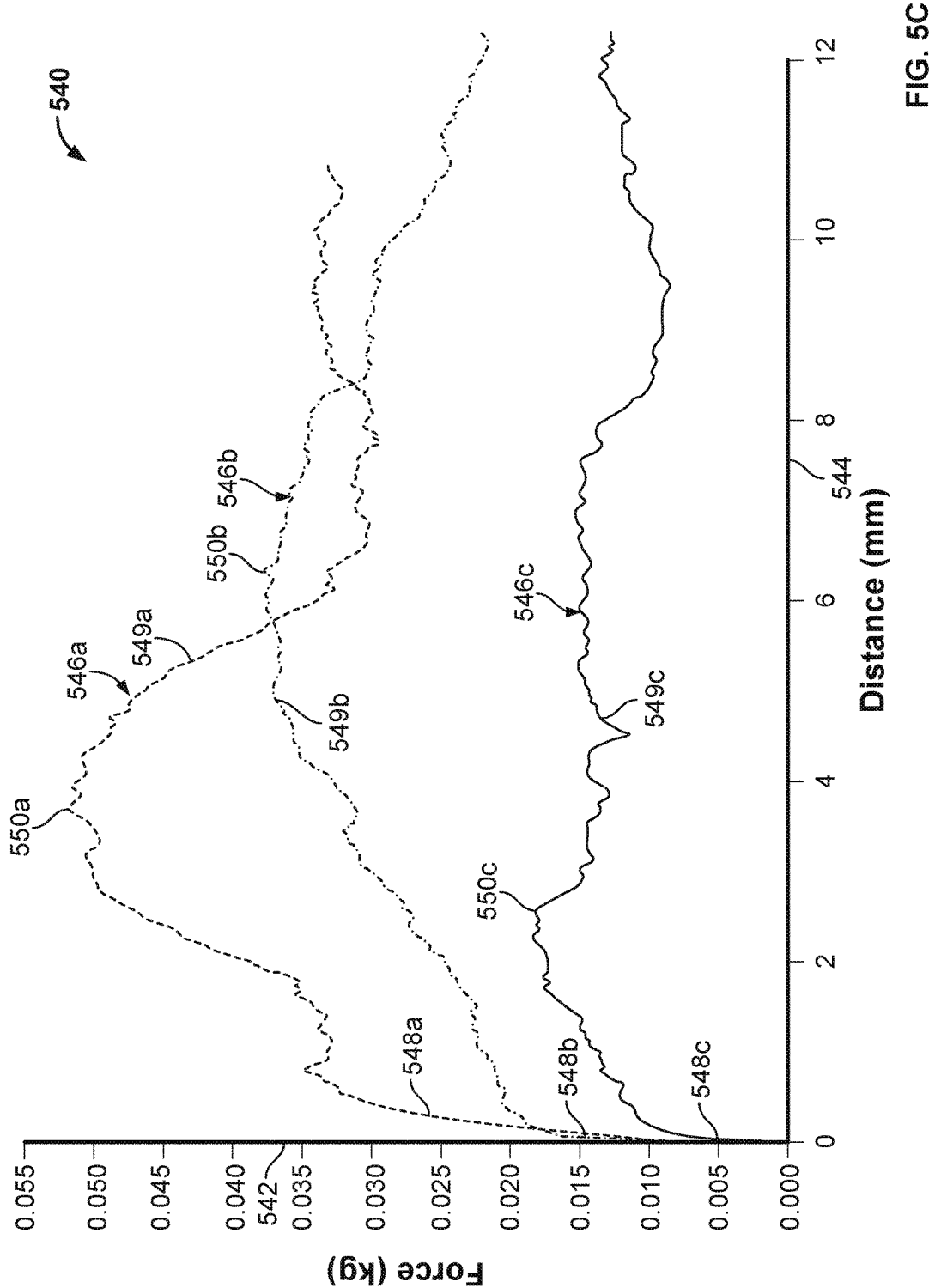

FIG. 5C shows the triplicate tests for the LSND mudcake and includes a y-axis 542 which represents force in kilograms, an x-axis 544 that represents distance in millimeters. Curves 546a-546c show the result of three independent implementations of method 400, including step 414. Each curve 546a-546c includes a respective linear portion 548a-548c, a respective non-linear portion 549a-549c, and a respective peak 550a-550c. A slope of a linear portion of the curves 546a-546c represents or approximates the SBM of the particular mudcake sample. The peak of the curves 546a-546c represents or approximates the USBS of the particular mudcake sample. In this implementation, mean values were determined from the curves 546a-546c to determine an average SBM (kgf/mm) and USBS (kgf) for the LSND mudcake sample.

Figure 5D:
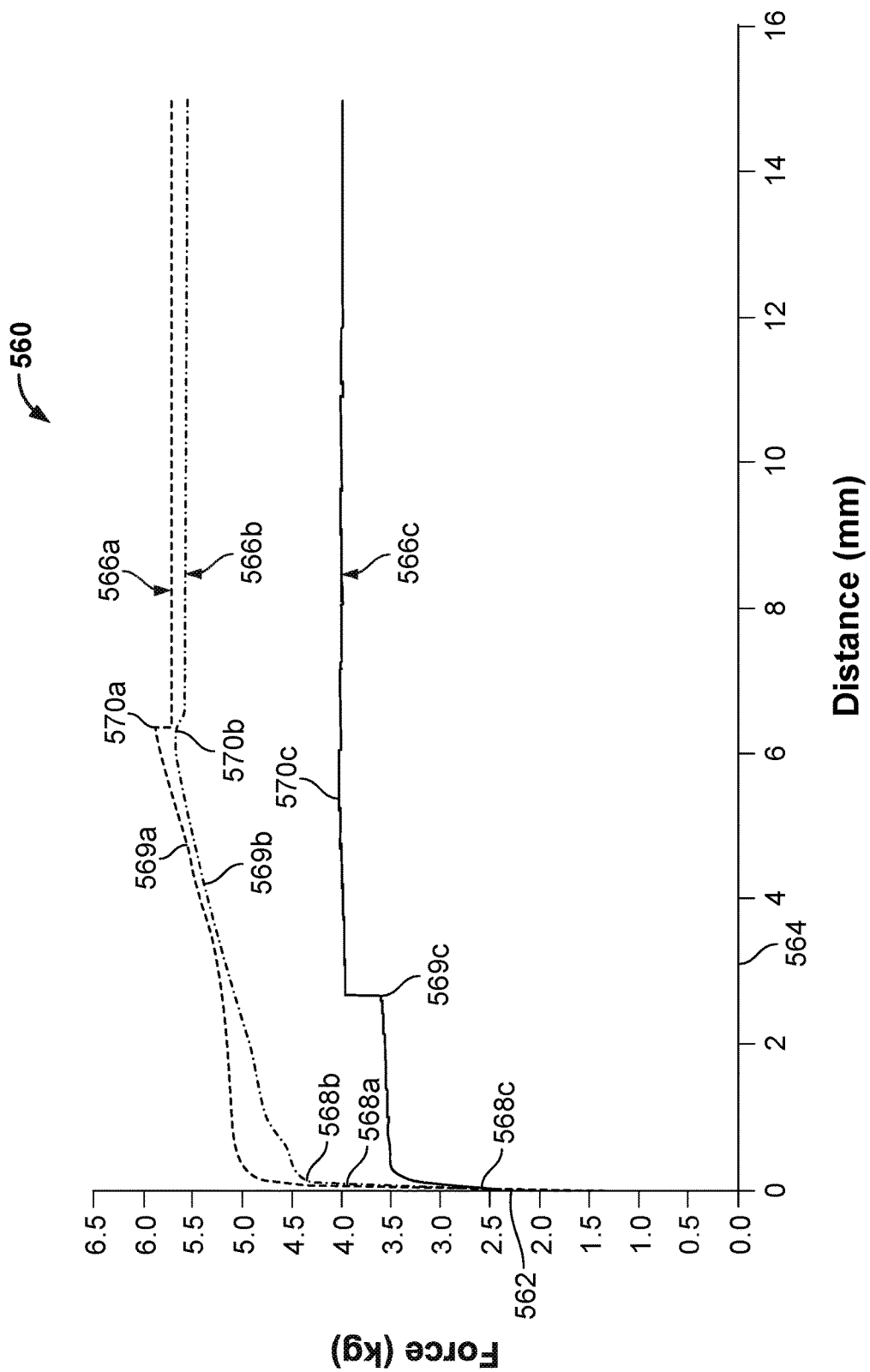

FIG. 5D shows the triplicate tests for the KCl polymer mudcake and includes a y-axis 562 which represents force in kilograms, an x-axis 564 that represents distance in millimeters. Curves 566a-566c show the result of three independent implementations of method 400, including step 414. Each curve 566a-566c includes a respective linear portion 568a-568c, a respective non-linear portion 569a-569c, and a respective peak 570a-570c. A slope of a linear portion of the curves 566a-566c represents or approximates the SBM of the particular mudcake sample. The peak of the curves 566a-566c represents or approximates the USBS of the particular mudcake sample. In this implementation, mean values were determined from the curves 566a-566c to determine an average SBM (kgf/mm) and USBS (kgf) for the KCl polymer mudcake sample.

As shown in FIGS. 5A-5D, the graphically recorded force versus displacement data indicates a linear response of the sticking bond for a short period at the start of the pulling test (for example, at step 408). After the short linear response, the data indicates a non-linear response under the applied load (for example, at step 410). The curves indicate that the damage or initiation of permanent deformation starts at the beginning of non-linear part of the experimental curve and ends at the termination of the nonlinear part of the curve when a critical extension point is reached. In some aspects, there is small variation in pulling force in the non-linear part of the curves due to progressive failure or damage to the sticking bonds. Compared to the initial linear part of the curves, there is a relatively larger elongation of the sticking bonds in this non-linear part of the curves.

Further, the graphically recorded force versus displacement data indicate some variation in the behavior of the same mudcake under the application of pulling force at the same displacement rate, as shown in that each of the triplicate tests for a similarly-composed mudcake sample has a unique curve. In some aspects, this is due, at least in part, to the fact that the formation of mudcake is neither highly ordered nor homogeneous and thus has regions of higher and lower bond densities at different parts of similarly-composed mudcakes. However, the mean value of the mudcake is a characteristic feature of the mudcake. Hence, in some aspects, mean values may be used in determining the sticking bond characteristics of the mudcake samples prepared according to step 402.

Method 400 may continue at step 416, which includes determining one or more properties of the mudcake sample based on the recorded force relative to the displacement distance. The determination may be made automatically (without request by a human user of the control system) or upon request to the control system. In some aspects, for example, the mudcake testing apparatus may detect the signal representative of the force and convert the signal representative of the force to a force value (as previously described), and then determine the one or more properties (for example, SBM and USBS). As described previously, these properties are determined by the mudcake testing apparatus according to the slope of the linear portion of the force versus displacement graph, and the peak of the force versus displacement graph, respectively.

In alternative aspects, the converted force values and displacement values may be presented to an operator (for example, tabularly or graphically), who then determines the one or more properties. As a further alternative, the signals representative of the force or the force values (or both) may be transmitted by the mudcake testing apparatus to a remote computing system (for example, located at a well operator home office, or a third party location) for determination of the one or more properties. The determined one or more properties can then be transmitted to the mudcake testing apparatus or exposed for viewing at the mudcake testing apparatus or other device that is communicable coupled to the remote computing system.

Figure 6A:
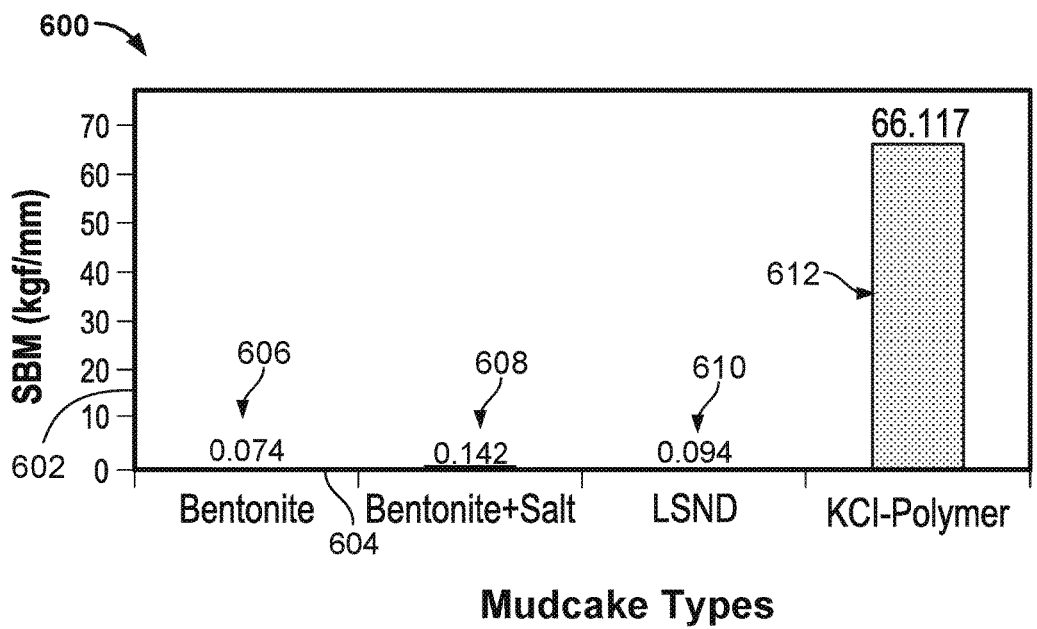
FIGS. 6A-6B are graphical representations that illustrate one or more properties of mudcake samples of specific compositions.
Figure 6B:
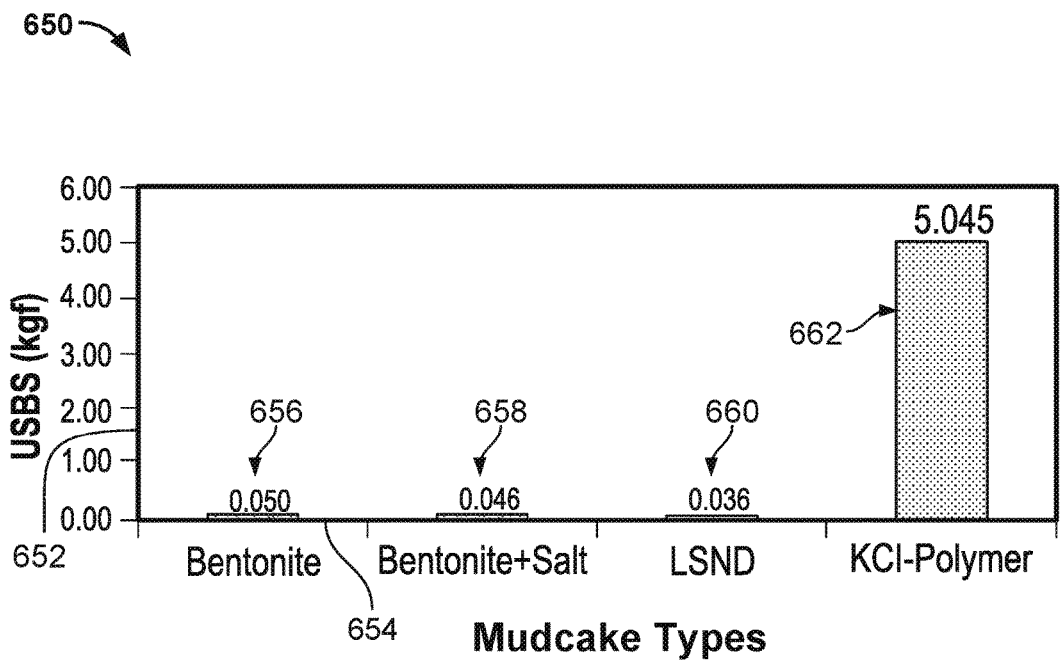

Turning briefly to FIGS. 6A-6B, bar graphs 600 and 650 illustrate the mean SBM and USBS for the four types of mudcake samples prepared according to step 402. Further, Tables 3 and 4 aggregate the data from FIGS. 5A-5D and 6A-6B.

TABLE 3

| Mudcake | SBM (Slope, kgf/mm) | | | Mean |
|---|---|---|---|---|
| Bentonite | 0.060 | 0.075 | 0.088 | 0.074 |
| Bentonite + Salt | 0.134 | 0.151 | 0.142 | 0.142 |
| LSND | 0.095 | 0.091 | 0.096 | 0.094 |
| KCl-Polymer | 68.68 | 66.28 | 63.39 | 66.117 |

TABLE 4

| Mudcake | USBS (Maximum, kgf) | | | Mean |
|---|---|---|---|---|
| Bentonite | 0.064 | 0.052 | 0.033 | 0.050 |
| Bentonite + Salt | 0.070 | 0.038 | 0.028 | 0.046 |
| LSND | 0.052 | 0.038 | 0.018 | 0.036 |
| KCl-Polymer | 5.580 | 5.520 | 4.000 | 5.045 |

As shown, bar graph 600 includes a y-axis 602 showing mean SBM in kgf/mm, an x-axis 604 showing mudcake type, and four bars 606-612 representing the mean SBM of the four mudcake types: bentonite, salt water bentonite, LSND, and KCl polymer, respectively. Bar graph 650 includes a y-axis 652 showing mean USBS in kgf/mm, an x-axis 654 showing mudcake type, and four bars 656-662 representing the mean USBS of the four mudcake types: bentonite, salt water bentonite, LSND, and KCl polymer, respectively.

Analyses of the mean SBM of the four mudcakes 606-612 shown in FIG. 6A indicates that the highest mean SBM value is for the KCl-Polymer mudcake 612, which contains barite as a weighting material, followed by the salt water+bentonite mudcake 608, and then the LSND mudcake 610. The bentonite mudcake 606 shows the lowest mean SBM value compared to the other mudcakes prepared and tested according to steps 402-412. The data, in some aspects, indicates that in case of a differential sticking problem (for example, of a wellbore tubular in a wellbore), sticking bonds are strongest in the presence of weighted KCl-Polymer mud and weakest in the presence of bentonite mud. The LSND mud has sticking bond modulus drastically lower than the KCl-Polymer mud and slightly lower than the salt water bentonite mud. Fresh water bentonite mudcake has SBM value lower than LSND mudcake but slightly higher than the salt water bentonite mudcake.

Thus, such data may indicate that the absence of any polymeric additives and weighting material in the bentonite and salt water bentonite muds may be a reason for producing sticking bonds with very low bond toughness. This may further indicate that an initiation of fracture damage in the sticking bonds occurs at a lower pulling force in the bentonite and salt water bentonite muds compared to KCl-Polymer muds. On the other hand, the presence of polymeric additives and barite weighting materials in the KCl-Polymer muds may produce sticking bonds with very high bond toughness. Hence, the forced required for initiation of fracture damage with the sticking bonds in the KCl-Polymer muds is significantly higher. This is reflected by the higher SBM value 612 for KCl-Polymer mud. Mudcake deposited by the LSND mud containing medium size calcium carbonate as the major bridging material also showed low SBM and thus may indicate weaker sticking bonds formation in the presence of $CaCO_3$. The data of FIG. 6B (for example, USBS data) may indicate that the presence of barite as the weighting material can increase the sticking bond strength significantly.

Engineering significance of this observation is that the ease of recovery of a stuck pipe will be more difficult in the presence of weighted KCl-Polymer mud due to the formation of stronger sticking bonds at the mudcake pipe interface. It will be much easier to recover a stuck pipe from the matrix of a saltwater-bentonite, LSND and bentonite mudcakes than the matrix of a KCl-Polymer mudcake as the sticking bonds of these mudcakes showed much lower pull resistance than the sticking bonds of the KCl-Polymer mudcake. The recovery of a stuck pipe in the presence of bentonite mudcake will be the easiest one due to the formation of the weakest sticking bonds. The presence of NaCl slightly enhanced the stiffness of the sticking bonds. This is reflected by a slight increase in the SBM of Saltwater-bentonite mudcake compared to the bentonite mudcake.

In some aspects, method 400 may include additional steps. For example, based on the results determined in step 414, the control system (for example, control system 110) may suggest or recommend a particular drilling fluid for a drilling operation. Also, based on the results determined in step 414, the control system may suggest or recommend a particular additive for a drilling fluid. In addition, based on the results determined in step 414, the control system may predict a potential hazard or problem (for example, a stuck pipe prediction) associated with a drilling or completion operation. Also, based on the results determined in step 414, the control system may predict an ease of recovery of a stuck pipe in a drilling or other operation.

Figure 7:
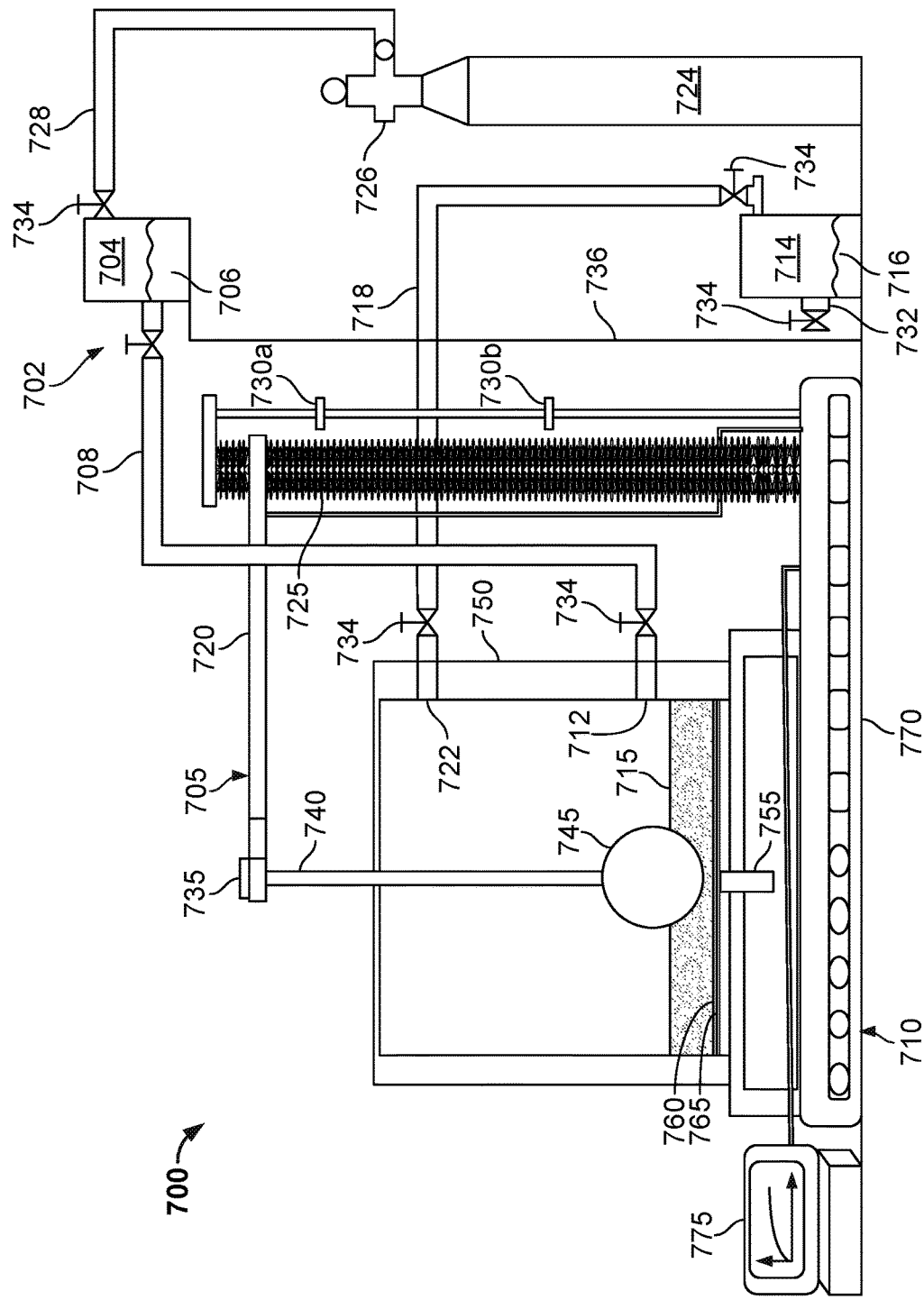
FIG. 7 is a schematic diagram of an implementation of a spotting fluid testing system.

FIG. 7 is a schematic diagram of an implementation of a spotting fluid testing system 700. The spotting fluid testing system 700 is used to test or validate a theoretical response of removing (for example, unsticking) of an object imbedded in a prepared mudcake sample. Thus, the system 700 may be used to test or validate a theoretical response to unsticking a portion of a wellbore tubular (for example, drill pipe or a portion of a drilling assembly) that is embedded in a mudcake of a wellbore.

The spotting fluid testing system 700 is similar to the mudcake testing system 100 shown in FIG. 1A, but also includes a spotting fluid testing assembly 702, as illustrated in FIG. 7. In example implementations, however, there may be components of mudcake testing system 100 that are not required in, or a part of, the spotting fluid testing system 700. Likewise, in example implementations, there may be components of spotting fluid testing system 700 that are not required in, or a part of, the mudcake testing system 100.

The illustrated implementation of the spotting fluid testing assembly 702 includes a feeder tank 704 that holds a volume of spotting fluid 706 to be tested in the spotting fluid testing system 700. The feeder tank 704 is fluidly coupled to a test cell 750 with an input conduit 708 that includes an inlet 712 into the cell 750. In the illustrated implementation, the feeder tank is supported by a stand 736, at a vertical level above the inlet 712. At this vertical level above the inlet 712, spotting fluid 706 may be fed through the input conduit 708, through the inlet 712, and into the test cell 750 by a gravity feed.

The spotting fluid testing assembly 702, in this implementation, also includes a collection tank 714 that can hold a volume of spent spotting fluid 716. The collection tank 714 is also fluidly coupled to the test cell 750 with an output conduit 718 that includes an outlet 722 from the cell 750. As shown, the collection tank 714 includes a drain 732.

As shown in FIG. 7, the inlet 712 is positioned vertically lower than the outlet 722 in the test cell 750. For example, this vertical difference may allow the entry of spotting fluid 706 and the exit of the spent spotting fluid 716 (or overflow spotting fluid 706) out when the top of the spotting fluid 706 reaches a pre-defined height. In some examples implementations, the top of spotting fluid 706 (for example, the location of the outlet 722) may be about 10 mm or more above the top of the mudcake sample 715-member 745 contact point to keep the mudcake sample 715 immersed in the spotting fluid 706 during tests.

The illustrated implementation of the spotting fluid testing assembly 702 also includes a gas cylinder 724 that holds a supply of pressurized gas therein. The gas cylinder 724 includes a pressure regulator 726 that controls a supply of pressurized gas 728 into the feed tank 704. For example, in some implementations, should gravity not be sufficient to circulate the spotting fluid from the feed tank 704 to the inlet 712, the pressurized gas 728 may be circulated into the feed tank 704 to force feed the spotting fluid 706 (for example, by an increase in pressure in the tank 704) from the tank 704, through the input conduit 708, through the inlet 712, and into the test cell 750. For example, the pressure regulator 726 fitted at an outlet of the gas cylinder 724 may allow the setting of a required pressure to push the spotting fluid 706 from the feeder tank 704 into the test cell 750.

The illustrated spotting fluid testing assembly 702 includes multiple valves 734 that are positioned within the assembly 702 to fluidly isolate or fluidly couple, when closed or opened, respectively, the components of the assembly 702. For example, one or more valves 736 are positioned in the input conduit 708 to regulate a flow of the spotting fluid 706 from the feed tank 704 into the test cell 750. One or more valves 736 are positioned in the output conduit 718 to regulate a flow of the spent spotting fluid 716 from the test cell 750 into the collection tank 714. Also, a valve 734 is positioned on the drain 732 to regulate a flow of the spent spotting fluid 716 from the collection tank 714 (for example, for recycling, purification, disposal or otherwise).

In some aspects, one or more of the valves 734 may be manually controlled to regulate a flow of fluid (for example, the spotting fluid 706, the spent spotting fluid 716, the pressurized gas 728, or otherwise) through the spotting fluid testing assembly 702. In alternative aspects, one or more of the valves 734 may be automatically controlled (for example, by the control system 710) to modulate to open or closed during operation of the spotting fluid testing assembly 702.

A mudcake sample 715, illustrated in FIG. 7, represents a portion of a mudcake in a wellbore that is developed during drilling or other wellbore operations. In this example implementation of the spotting fluid testing assembly 702, the mudcake sample 715 may be prepared identical to, or substantially identical to, the mudcake sample 115 as described with reference to FIGS. 1A-1B. Generally, the mudcake sample 715 represents residue deposited on a permeable medium (for example, a wellbore wall) that develops when drilling fluid is deposited against the wellbore wall under pressure. Because liquid is able to pass through the permeable medium, a sticky substance, called a "mudcake," may be left to form on the wellbore wall. The mudcake has certain properties based on, for instance, the drilling fluid used in the drilling operation. Such properties relate to the thickness (for example, which affects hydrocarbon production), toughness, slickness (for example, which affects an affinity to adhere or not to tubular drilling components), and permeability (for example, also affecting production). Mudcakes that form on permeable zones in the wellbore can cause stuck pipe and other drilling problems. Thus, the testing system 700 can be used to determine one or more properties of the spotting fluid 706 that can reduce an adhesion of a mudcake to, for example, a wellbore wall. The determination of such properties of the spotting fluid 706 may be used to select a particular spotting fluid to use for an unsticking operation (for example, to free a stuck pipe from a wellbore).

The illustrated implementation of the spotting fluid testing system 700 includes a load cell 705 that is communicably coupled to the control system 710. Several example load cells may be used as the load cell 705, including, without limitation, a uniaxial load cell, a triaxial load cell, a biaxial load cell, a strain-gauge load cell, a hydraulic load cell, or a pneumatic load cell. In some aspects, the load cell 705 is capable of applying 50 kilograms-force (kgf) or less of force in operation of the system 700.

The load cell 705 includes carrier arm 720 mounted on a load stand 725. The load stand 725 operates to lower and raise the carrier arm 720, and by extension a testing member 745 mounted on a test leg 740 coupled to the carrier arm 720, with a variable mount of force. As illustrated in this implementation, an upper position limiter 730a and a lower position limiter 730b is mounted adjacent the load stand 725 to provide upper and lower movement limits of the carrier arm 720 during operation of the spotting fluid testing system 700.

The spotting fluid testing system 700 also includes the test cell 750. In some aspects, the test cell 750 can be similar or identical to the test cell 150, for example, an API test cell or high temperature-high pressure (HTHP) test cell into which a prepared mudcake sample 715 is placed. Example test cells can include: a Faring Instrument No. 101502980 or No. 101533370; an OFI Testing Equipment, Inc. 140-40 Water Loss Press 4 Unit, serial #14-15; or an OFI Testing Equipment, Inc. 170-00 OFITE HTHP Press, Single End Test Cell. In alternative aspects, the test cell 750 and the test cell 150 may be different test cells. For instance, the test cell 750 may have the same or similar inner and outer dimensions (for example, diameter, or width and length) as the test cell 150 but a lower height than the test cell 150.

In this implementation, the mudcake sample 715 is placed on top of a filter 760, which in turn is placed on top of a screen 765 (for example, metallic screen). The illustrated test cell 750 includes an outlet 755 positioned at a bottom, for example, to allow liquid to drain from the mudcake sample 715 if necessary.

The illustrated control system 710, in this implementation, comprises a processor based controller 770 (for example, CPU) that is communicably coupled to a data logger 775. The controller 770 includes an input peripheral (for example, keyboard, toggles, button, mouse, or otherwise) for use by an operator (for example, to input operational constraints) as well as an output peripheral. The controller 770 is coupled with the load cell 705 (for example, through one or more wires or wirelessly) to receive data output from the load cell 705 during operation of the spotting fluid testing system 700. For example, data such as force applied by the load stand 725 (for example, upward) on the member 745 (for example, through the carrier arm 720 and the leg 740), as well as position of the member 745 (for example, initial position in contact in the mudcake sample 715, relative distance of the member 745 from an initial position, or both), may be transmitted to or received by the controller 770.

The implementation of the load cell 705 includes a calibration platform 735. The calibration platform 735 receives a signal from the load cell 705 that represents the force applied on the test member 745 during operation of the testing system 700. The calibration platform 735 then calculates a relationship between the detected signal and the force. For example, the load cell 705 detects and measures an electrical resistance signal that is proportional to the force applied to the test member 745. The electrical resistance signal is then converted to a force signal to be output by the control system 710.

The data logger 775 includes an output device for display of the data (for example, force, displacement distance, or other data) sent to the controller 770 from the load cell 705. Example outputs include graphical representations of force versus displacement curves are shown for various spotting fluids 706 in FIGS. 9A-9C and 10A-10C.

As is shown in FIG. 2 with respect to the mudcake sample 150, the mudcake sample 715 experiences an interface between the member 745 and the sample 715. More specifically bonds develop once the member 745 is inserted into the mudcake sample 715 that is positioned in the test cell 750. Generally, once an object, such as the member 745 that represents a wellbore tubular, is embedded into a matrix of a mudcake (for example, the mudcake sample 715), adhesive bonds develop between the object and the mudcake interface due to the alteration of free surface energy at the contacting surfaces of the mudcake sample 715 and the embedded object (for example, the member 745). The sticking bonds are the combined results of adhesive and cohesive bonds and are governed by the resultant effect of interfacial tension, Vander der Waal forces, inter-atomic and inter-molecular forces, hydrogen and ionic bonds, and otherwise.

As the magnitude of these forces varies depending on the composition of the mudcake sample 715, physics and chemistry of the drilling fluid and drilling fluid additives and also the physics and chemistry of the base fluid used in preparing the drilling fluid, mudcakes deposited by various drilling systems have significantly different sticking bond characteristics. Such characteristics are sticking bond modulus (SBM) (for example, a rate of increase of a pull resistance of a mudcake) and ultimate sticking bond strength (USBS). The higher the strength of the surface tension, molecular and atomic forces, strength of ionic and hydrogen bondings, the stronger the sticking bonds between the member 745-mudcake sample 715 interface. As the sticking bonds are stronger, a higher pulling force (for example, by the load stand 725) is required to unstick the member 745 from the mudcake sample 715. Likewise, in wellbore operations, as the sticking bonds between a wellbore mudcake and wellbore tubular become stronger, a higher pulling force (for example, by a drill string) is required to unstick the wellbore tubular from the wellbore mudcake.

The member 745 embedded into mudcake sample 715 experiences interfacial adhesive bonds and cohesive matrix bonds that adhere the member 745 with the mudcake sample 715 (examples of such bonds are shown in FIG. 2 with respect to the sample 115). If such adhesive bonds and cohesive bonds are weak, then the member 745 is released more easily based on an upward force applied to the member 745 from the load stand 725 (for example, pulling the member 745 out of the sample 715). On the other hand, a mudcake sample 715 that creates strong adhesive bonds and cohesive bonds at the mudcake-member interface may require a higher upward pull (for example, by the load stand 725) to release from the mudcake sample 715.

As illustrated in the implementation of the spotting fluid testing system 700 shown in FIG. 7, the member 745 comprises a spherically-shaped member. Other implementations of a mudcake testing system according to the present disclosure may include alternatively-shaped members, such as cylindrical, egg-shaped, or otherwise. In some aspects, the spherical member 745 is used to more accurately determine one or more properties (for example, SBM, USBS, or otherwise) of the mudcake sample 715 as compared to, for example, a tubular or cylindrically-shaped member. For instance, even though a wellbore component that sticks to a wellbore mudcake is typically cylindrical in cross section (for example, drill pipe, a drill string, or other tubular component), use of a cylindrical member may not provide accurate readings due to the sharp edges that would be present on a cylindrical member. In short, the spherical member 745, in some aspects, may better represent a wellbore tubular for more accurate determination of the mudcake properties.

In an example operation of the spotting fluid testing assembly 702, the mudcake sample 715 is prepared, for example, according to the description of the preparation of the mudcake sample 115. For example, the mudcake sample 715 may be prepared to more than 10 mm thickness, for instance, in the test cell 150. Further, the mudcake sample 715 may not be prepared with a minimum filtration time of 30 minutes per API procedure, but instead, for example, the filtration time may be set longer to achieve the 10 mm thickness.

Next, the mudcake sample 715 may be placed in the test cell 750 (for example, if not prepared in the test cell 750). In some aspects, should the mudcake sample 715 be prepared in another test cell, such as test cell 150, the sample 715 may be washed gently with fresh water to remove the soft jelly-like mud material from the top of the mudcake sample 715 prior to placement in the test cell 750.

Next, operating parameters for the test of the spotting fluid 706 may be set. For example, the control system 710 may be used to set all test parameters, record and plot the test data graphically, set the initial load and displacement reading to zero and define the rate of compression for embedding the member 745 into the mudcake sample 715, as well as set the pulling rate during a test. In some examples, a pulling rate of 0.02 mm/sec may be used during the embedment and pulling phases of the test.

After setting the operating parameters, the member 745 is embedded (for example, automatically) into the mudcake matrix using a controlled downward displacement of the spherical member 745 (for example, at a rate of 0.02 mm/sec) until a particular embedment depth of the member 745 into the mudcake sample 715 is reached. In some aspects, the embedment depth may be about 5 mm.

After the embedment of the member 745, a particular time duration (for example, about 2 minutes) may pass in order to stabilize the position of the member 745, the mudcake sample 715-member 745 interface, and the mudcake matrix material. At this point, the initial load and the starting depth are set at zero for the test. This step of the test may simulate the sticking event of a drill string into the mudcake matrix in a real wellbore environment.

After the embedment of the member 745 into the mudcake sample 715 (and, in some aspects, waiting for the stabilization time to pass), the spotting fluid 716 is circulated into the spotting fluid test cell 750. In some aspects, a particular depth of spotting fluid 716 may be achieved, such as, for example, until the top of the spotting fluid 706 reaches 10-15 mm above the top of the mudcake sample 715. If the spotting fluid 706 reaches the outlet 722, the fluid 706 may exit through the outlet 722 to collect into the collection tank 714. This step simulates the placement of spotting fluid in a stuck pipe zone in a wellbore.

In some example operations of the spotting fluid testing assembly 702, the spotting fluid 706 in the test cell 750 (and on top of the mudcake sample 715) may be allowed a particular time duration to soak into the sample 715. In some aspects, allowing a soaking time for the spotting fluid 706 may de-bond, degrade, or damage the adhesive and cohesive forces causing sticking of the member 745 to the mudcake 715. For example, the particular time duration may be minutes, hours, days, or even longer. In some examples, the time duration may be between 5 and 20 hours, 12 and 16 hours, or other time duration.

After completion of the soaking time (if any), an application of pulling force on the member 745 away from the mudcake sample 715 may be initiated. In some aspects, a constant pulling rate (for example, of 0.02 mm/sec) may be applied during the upward displacement of the embedded member 745. During the application of the pulling force, a force versus displacement curve may be recorded automatically by the control system 710 that also controls the operation of the apparatus during the test. The control system 710 may also record all test data and display the data on-screen in a graphical format. In some aspects, the operation may be terminated after recording a maximum pulling force and the recovery of the member 745 from the mudcake sample 715.

Figure 8:
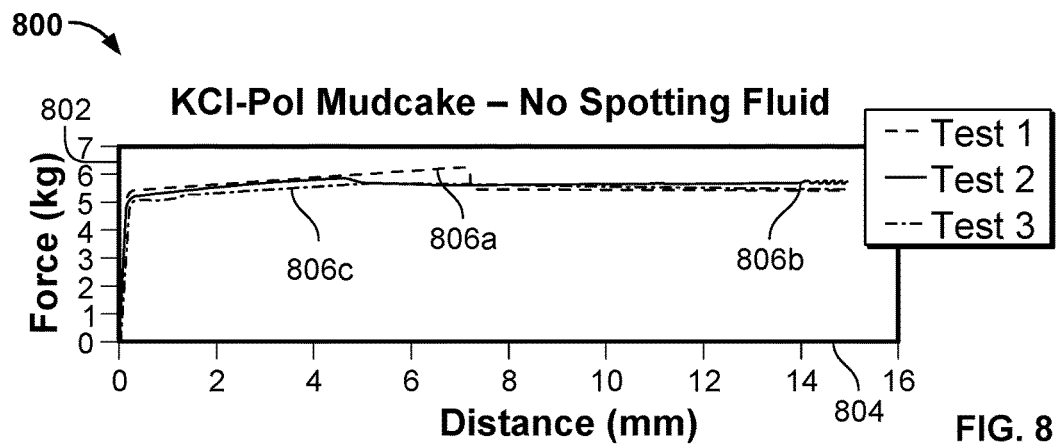
FIG. 8 is a graphical representation that illustrates a pulling force relative to upward displacement during testing of a mudcake without application of a spotting fluid.

An embodiment of the described spotting fluid testing system 700, along with the spotting fluid testing assembly 702, was used to test several different spotting fluids to determine one or properties of the fluids in experimental testing. The spotting fluids used in the experimental tests are described in Table 5. Each particular spotting fluid (numbered 1, 2, and 3) was used in a test operation (as described previously), and each particular spotting fluid was tested at two particular soaking times: 6 hours and 16 hours. The prepared mudcake sample used during the testing of the spotting fluid testing assembly 702 was a KCl-Polymer mudcake as described in Table 2. The graphical results of the experimental tests are shown in the force versus displacement curves of FIGS. 9A-9C (for the 6 hour soaking time) and FIGS. 10A-10C (for the 16 hour soaking time). Also, a baseline test was performed using no spotting fluid, which results are shown in FIG. 8. Each test was performed in triplicate: Test 1, Test 2, and Test 3.

TABLE 5

| Components | Field Formulation (bbl.) | Concentration (%) | Lab Formulation (mL) |
|---|---|---|---|
| Spotting Fluid #1 | | | |
| Diesel | 64 | 0.64 | 224.34 |
| EZ-SPOT | 7.85 | 0.08 | 27.52 |
| Water | 28 | 0.28 | 98.15 |
| Total Volume | 99.85 | | 350.00 |
| Spotting Fluid #2 | | | |
| Water | 28 | 0.28 | 98.15 |
| Total Volume | 99.85 | | 350.00 |
| Pipe-Lax | 7.85 | 0.08 | 27.52 |
| Water | 28 | 0.28 | 98.15 |
| Total Volume | 99.85 | | 350.00 |
| Spotting Fluid #3 | | | |
| Glycol | 85.1 | 0.80 | 280.91 |
| Lubricant | 15.7 | 0.15 | 51.82 |
| Pipe-Lax | 5.23 | 0.05 | 17.26 |
| Total Volume | 106.03 | | 350.00 |

In Table 5, both field and lab formulations are described. In the field formulation, the spotting fluid is designed based on concentration of additives required for one or 100 barrels of the spotting fluid final product. In the field formulation, the liquid additive concentrations are in barrel or gallon and the solids additive concentrations are in pounds (lbs). In the lab formulation, 350 cubic centimeters (cc) or its multiples are produced by adding solids and/or liquid components of a spotting fluid formulation. Here, the liquid is in cubic centimeters and the solids are measured in grams (gm). A gram of solid additive in a lab formulation mixed with 350 cc spotting fluid in the lab equals to the pounds of solids product in one (1) barrel of spotting fluid in the field. For example, 1 gm in the lab will be equivalent to 1 pound in the field. Further, several of the components (for example, EZ-SPOT, Pipe Lax) refer to product names known in the oil and gas industry.

FIG. 8 is a graphical representation that illustrates a pulling force relative to upward displacement during testing of the KCl-Polymer mudcake sample without application of a spotting fluid. For example, first a pulling test without a spotting fluid in the spotting fluid test cell was performed to get a bench mark value of SBM and the ultimate sticking bond strength of the mudcake sample. This step of the test simulates the attempt to recover a stuck pipe without placing a spotting fluid, which may or may not be successful depending on the strength of the sticking bonds formed between the mudcake and pipe contact surfaces. The characteristic values of the original mudcake was then used to evaluate the performance of various spotting fluids by determining the % reduction in SBM and the USBS of the mudcake sample due to de-bonding, dehydration, damaging, and lubricating effect of the spotting fluid.

FIG. 8 shows a graph 800 of the triplicate tests for the KCl polymer mudcake tested without spotting fluid, and includes a y-axis 802 which represents force in kilograms, and an x-axis 804 that represents pull distance, in millimeters, of the member from an initial position embedded in the mudcake sample. Curves 806a-806c show the result of three independent implementations of the test operation, which, without spotting fluid, may be similar or identical to method 400 described previously. The numerical results of the triplicate tests shown in plots 806a-806c are shown in Table 6.

TABLE 6

| Test No. | Correlation Coefficient | SBM (Slope) kgf/mm | USBS (Max Pulling Force) Kgf |
|---|---|---|---|
| Test 1 | 0.999 | 40.73 | 6.35 |
| Test 2 | 0.997 | 36.93 | 5.93 |
| Test 3 | 0.997 | 37.07 | 5.76 |
| Average: | — | 38.24 | 6.01 |
| S.D. | — | 2.16 | 0.30 |
| Coeff. of Variation | — | 5.64 | 5.00 |

Figure 9A:
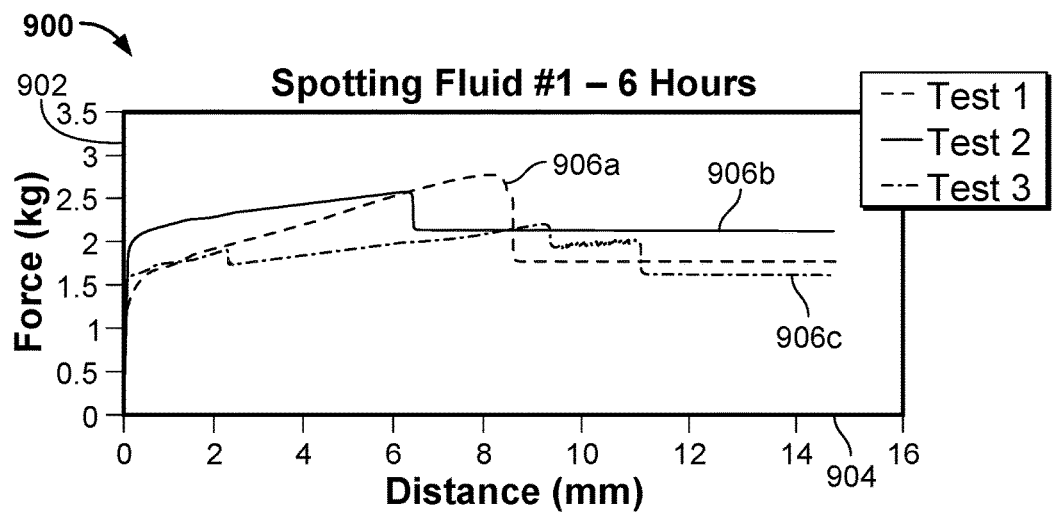
FIGS. 9A-9C are graphical representations that illustrate one or more properties of different spotting fluids applied to a mudcake sample for a particular time duration.
Figure 9B:
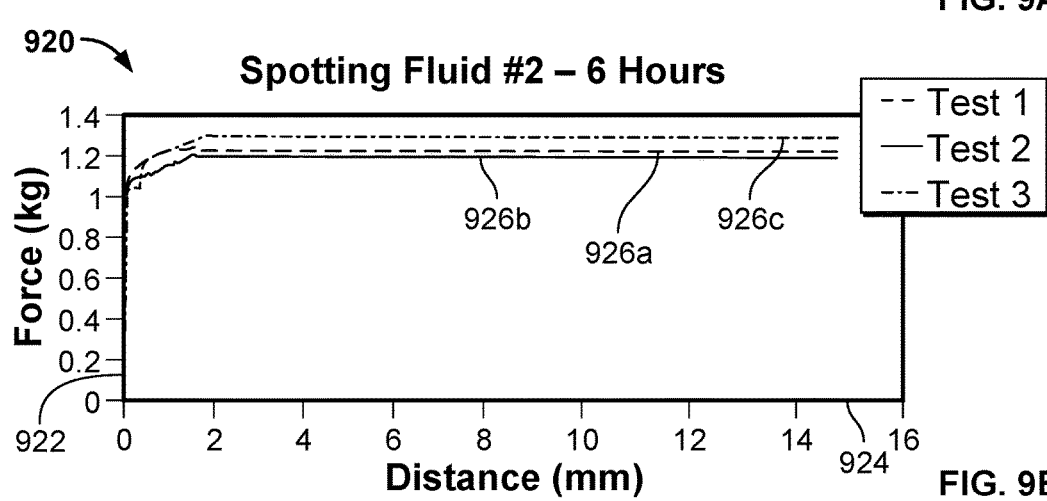
Figure 9C:
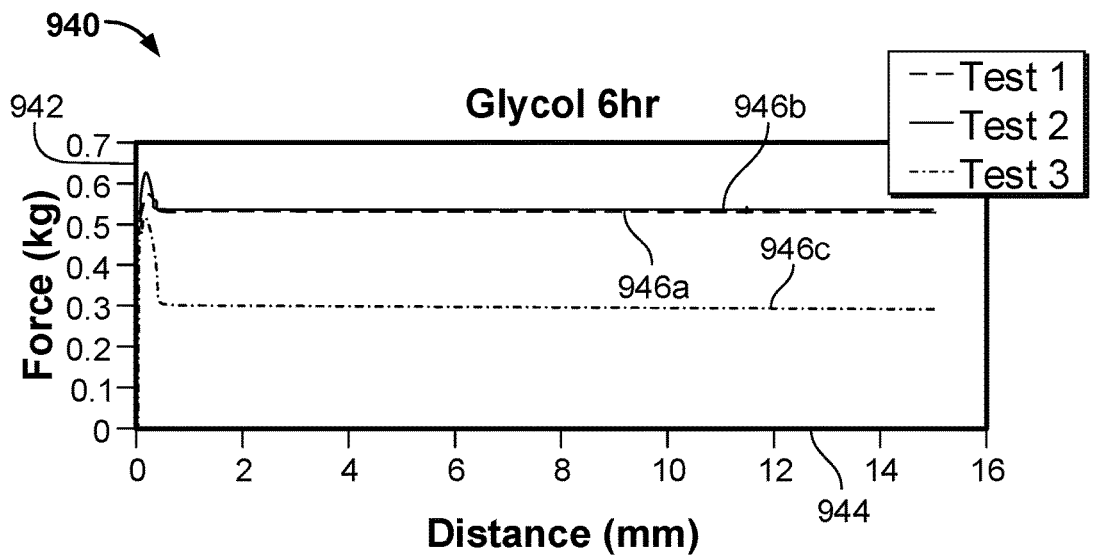

FIGS. 9A-9C are graphical representations that illustrate results of a pulling test (performed in triplicate) in which Spotting Fluids 1, 2, and 3 (described in Table 5) have been applied to a mudcake sample, which has subsequently been soaked with the particular spotting fluid for 6 hours prior to initiation of each pulling test. Turning to graph 900 in FIG. 9A, this graph illustrates a triplicate test of Spotting Fluid #1, after soaking the KCl-Polymer mudcake sample for 6 hours. Graph 900 includes a y-axis 902 which represents force in kilograms, and an x-axis 904 that represents pull distance, in millimeters, of the member from an initial position embedded in the mudcake sample. Curves 906a-906c show the result of three independent implementations of the test operation, described with reference to FIG. 7 and the spotting fluid testing system 700. The numerical results of the triplicate tests shown in plots 906a-906c are shown in Table 7.

TABLE 7

| Test No. | Correlation Coefficient | SBM (Slope) kgf/mm | USBS (Max Pulling Force) Kgf |
|---|---|---|---|
| Test 1 | 0.991 | 33.349 | 3.11 |
| Test 2 | 0.992 | 33.186 | 2.87 |
| Test 3 | 0.974 | 35.213 | 2.46 |
| Average: | — | 33.92 | 2.81 |
| S.D. | — | 1.13 | 0.33 |
| Coeff. of Variation | — | 3.33 | 11.74 |

Turning to graph 920 in FIG. 9B, this graph illustrates a triplicate test of Spotting Fluid #2, after soaking the KCl-Polymer mudcake sample for 6 hours. Graph 920 includes a y-axis 922 which represents force in kilograms, and an x-axis 924 that represents pull distance, in millimeters, of the member from an initial position embedded in the mudcake sample. Curves 926a-926c show the result of three independent implementations of the test operation, described with reference to FIG. 7 and the spotting fluid testing system 700. The numerical results of the triplicate tests shown in plots 926a-926c are shown in Table 8.

TABLE 8

| Test No. | Correlation Coefficient | SBM (Slope) kgf/mm | USBS (Max Pulling Force) Kgf |
|---|---|---|---|
| Test 1 | 0.983 | 22.35 | 1.26 |
| Test 2 | 0.984 | 21.08 | 1.23 |
| Test 3 | 0.989 | 24.61 | 1.32 |
| Average: | — | 22.68 | 1.27 |
| S.D. | — | 1.79 | 0.047 |
| Coeff. of Variation | — | 7.89 | 3.69 |

Turning to graph 940 in FIG. 9C, this graph illustrates a triplicate test of Spotting Fluid #3, after soaking the KCl-Polymer mudcake sample for 6 hours. Graph 940 includes a y-axis 942 which represents force in kilograms, and an x-axis 944 that represents pull distance, in millimeters, of the member from an initial position embedded in the mudcake sample. Curves 946a-946c show the result of three independent implementations of the test operation, described with reference to FIG. 7 and the spotting fluid testing system 700. The numerical results of the triplicate tests shown in plots 946a-946c are shown in Table 9.

TABLE 9

| Test No. | Correlation Coefficient | SBM (Slope) kgf/mm | USBS (Max Pulling Force) kgf |
|---|---|---|---|
| Test 1 | 0.990 | 20.120 | 0.583 |
| Test 2 | 0.972 | 21.204 | 0.636 |
| Test 3 | 0.983 | 23.634 | 0.578 |
| Average: | — | 21.653 | 0.599 |

TABLE 9-continued

| Test No. | Correlation Coefficient | SBM (Slope) kgf/mm | USBS (Max Pulling Force) kgf |
|---|---|---|---|
| S.D. | — | 1.799 | 0.032 |
| Coeff. of Variation | — | 8.31 | 5.34 |

Figure 10A:
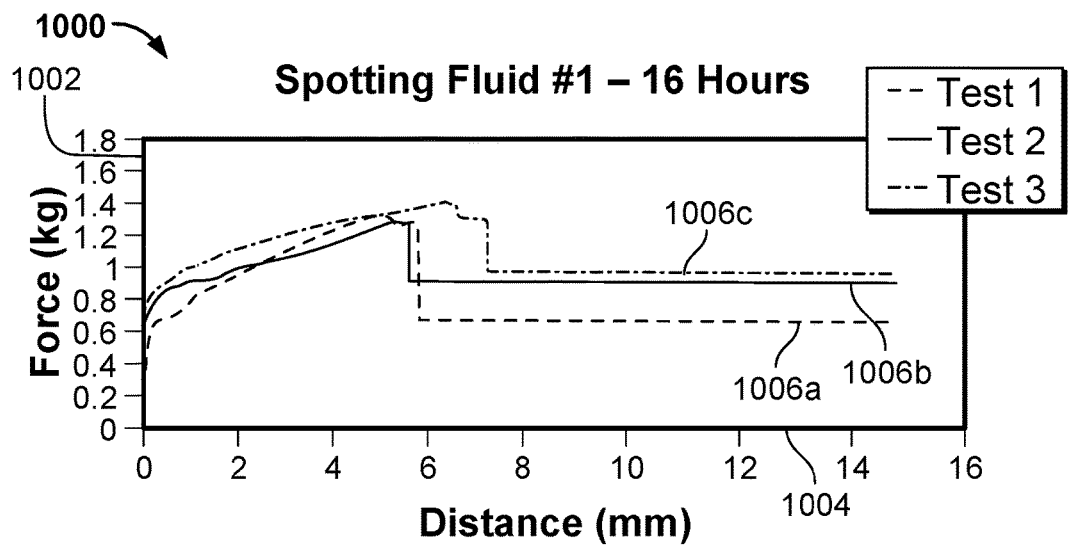
FIGS. 10A-10C are graphical representations that illustrate one or more properties of different spotting fluids applied to a mudcake sample for another particular time duration.
Figure 10B:
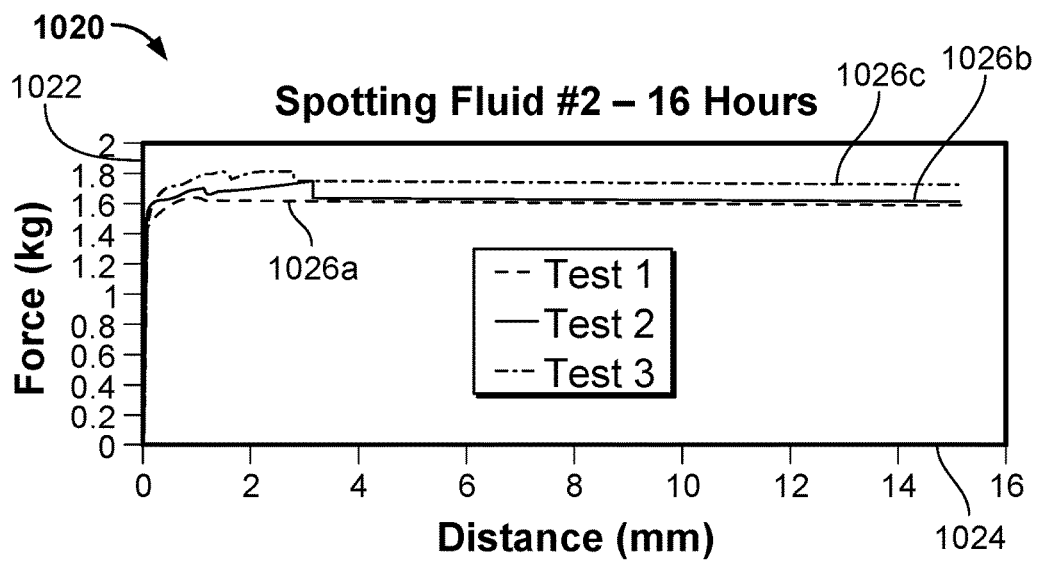
Figure 10C:
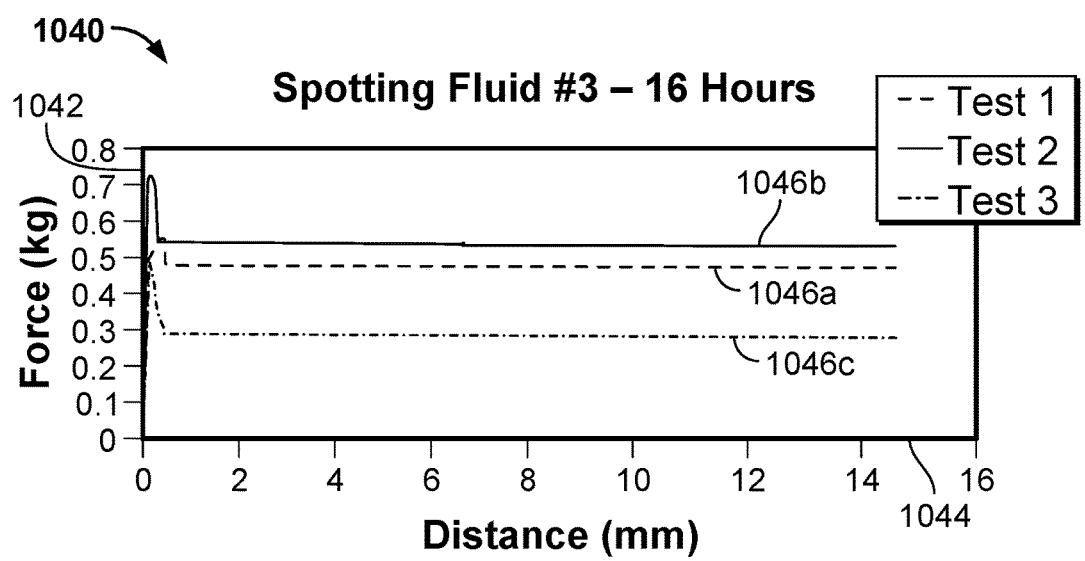

FIGS. 10A-10C are graphical representations that illustrate results of a pulling test (performed in triplicate) in which Spotting Fluids 1, 2, and 3 (described in Table 5) have been applied to a mudcake sample, which has subsequently been soaked with the particular spotting fluid for 16 hours prior to initiation of each pulling test. Turning to graph 1000 in FIG. 10A, this graph illustrates a triplicate test of Spotting Fluid #1, after soaking the KCl-Polymer mudcake sample for 16 hours. Graph 1000 includes a y-axis 1002 which represents force in kilograms, and an x-axis 1004 that represents pull distance, in millimeters, of the member from an initial position embedded in the mudcake sample. Curves 1006a-1006c show the result of three independent implementations of the test operation, described with reference to FIG. 7 and the spotting fluid testing system 700. The numerical results of the triplicate tests shown in plots 1006a-1006c are shown in Table 10.

TABLE 10

| Test No. | Correlation Coefficient | SBM (Slope) kgf/mm | USBS (Max Pulling Force) kgf |
|---|---|---|---|
| Test 1 | 0.992 | 17.11 | 1.49 |
| Test 2 | 0.985 | 24.65 | 1.43 |
| Test 3 | 0.990 | 25.07 | 1.57 |
| Average: | — | 22.28 | 1.50 |
| S.D. | — | 4.48 | 0.069 |
| Coeff. of Variation | — | 20.12 | 4.61 |

Turning to graph 1020 in FIG. 10B, this graph illustrates a triplicate test of Spotting Fluid #2, after soaking the KCl-Polymer mudcake sample for 16 hours. Graph 1020 includes a y-axis 1022 which represents force in kilograms, and an x-axis 1024 that represents pull distance, in millimeters, of the member from an initial position embedded in the mudcake sample. Curves 1026a-1026c show the result of three independent implementations of the test operation, described with reference to FIG. 7 and the spotting fluid testing system 700. The numerical results of the triplicate tests shown in plots 1026a-1026c are shown in Table 11.

TABLE 11

| Test No. | Correlation Coefficient | SBM (Slope) kgf/mm | USBS (Max Pulling Force) kgf |
|---|---|---|---|
| Test 1 | 0.993 | 28.835 | 1.825 |
| Test 2 | 0.993 | 30.706 | 1.758 |
| Test 3 | 0.994 | 31.739 | 1.653 |
| Average: | — | 30.427 | 1.745 |
| S.D. | — | 1.472 | 0.087 |
| Coeff. of Variation | — | 4.84 | 4.98 |

Turning to graph 1040 in FIG. 10C, this graph illustrates a triplicate test of Spotting Fluid #3, after soaking the KCl-Polymer mudcake sample for 16 hours. Graph 1040 includes a y-axis 1042 which represents force in kilograms, and an x-axis 1044 that represents pull distance, in millimeters, of the member from an initial position embedded in the mudcake sample. Curves 1046a-1046c show the result of three independent implementations of the test operation, described with reference to FIG. 7 and the spotting fluid testing system 700. The numerical results of the triplicate tests shown in plots 1046a-1046c are shown in Table 12.

TABLE 12

| Test No. | Correlation Coefficient | SBM (Slope) kgf/mm | USBS (Max Pulling Force) Kgf |
|---|---|---|---|
| Test 1 | 0.988 | 23.765 | 0.560 |
| Test 2 | 0.982 | 25.346 | 0.727 |
| Test 3 | 0.970 | 20.113 | 0.500 |
| Average: | — | 23.075 | 0.596 |
| S.D. | — | 2.684 | 0.118 |
| Coeff. of Variation | — | 11.63 | 19.80 |

In Tables 6-12, the column labeled "Correlation Coefficient" includes numerical values between 0 and 1. A Correlation Coefficient, in this example, indicates the significance of test for relationship between two continuous variables. It indicates the strength of relationship between the parameters. The higher the Correlation Coefficient, better the relationship between the two test parameters. A correlation value of greater than 0.9 is considered very strong relation. A perfect relation between two test parameters is indicated by a Correlation Coefficient equal to 1. In this example, the Correlation Coefficient indicates the significance of the relationship between the SBM and the USBS for the triplicate tests.

Table 13 shows the average SBM and USBS values and percentage reduction of such values relative to the same variables that resulted from the "no spotting fluid" test described in FIG. 8 and Table 6.

TABLE 13

| Spotting Fluid-Soak Time | Average SBM (kgf/mm) | Average USBS (kgf) | SBM Reduction (%) | USBS Reduction (%) |
|---|---|---|---|---|
| None-NA | 38.24 | 6.010 | — | — |
| Spotting Fluid #1 - 6 hr. | 33.92 | 2.810 | 11.30 | 53.24 |
| Spotting Fluid #2 - 6 hr. | 22.68 | 1.270 | 40.69 | 78.87 |
| Spotting Fluid #3 - 6 hr. | 21.65 | 0.600 | 43.38 | 90.02 |
| Spotting Fluid #1 - 16 hr. | 22.28 | 1.500 | 41.74 | 75.04 |
| Spotting Fluid #2 - 16 hr. | 30.43 | 1.750 | 20.42 | 70.88 |
| Spotting Fluid #3 - 16 hr. | 23.08 | 0.596 | 39.64 | 90.08 |

As shown from the load displacement curves of recovering the member from the mudcake sample in the tests without spotting fluid (for example, shown in FIG. 8 and Table 6) and the tests with spotting fluid (for example, shown in FIGS. 9A-9C and 10A-10C and Tables 7-12), there is a much higher required pulling force to unstick the member from the mudcake without spotting fluid relative to the pulling force required to unstick the member from the mudcake with spotting fluid. The mudcake samples tested with results in graph 800 and Table 6 indicate a USBS of 6 kgf and a SBM of 38.24 kgf/mm. However, mudcake samples tested with one of the Spotting Fluids #1, 2, or 3 showed much lower SBM and USBS after 6 and 16 hours soaking time. This is due to, for example, the damaging and degradation action of the spotting fluids on the sticking (adhesive-cohesive) bonds that bind the spherical ball to the mudcake matrix.

The tests curves generated after 6 hours of soaking time in the presence of Spotting Fluid #1 gave an average SBM value of 33.92 kgf/mm and an average USBS value of 2.81 kgf. However, the curves generated after 16 hour of soaking time gave an average SBM value of 22.28 kgf/mm and an average USBS value of 1.5 kgf. Calculation of a percent reduction of SBM and the USBS indicates more than 11 and 53% reduction of SBM and USBS values after 6 hours of soaking time relative to such values of the non-spotting fluid tests. On the other hand, calculation of a percent reduction of SBM and USBS after 16 hours soaking time indicates more than a 41 and 75% reduction of SBM and the USBS respectively. The data may, therefore, indicate that the Spotting Fluid #1 may reduce the SBM and USBS of the mudcakes significantly after 6 and 16 hours of soaking time. As the tests indicate significantly higher reduction of SBM and USBS after 16 hours soaking time than 6 hours soaking time, the 6 hours soaking time may not be sufficient enough for complete interaction in the presence of Spotting Fluid #1. This result may also indicate a requirement of a longer time of interactions for the Spotting Fluid #1 to damage and degrade the sticking bonds.

The tests curves generated after 6 hour of soaking time in the presence of Spotting Fluid #2 gave an average SBM value of 22.68 kgf/mm and an average USBS value of 1.27 kgf. However, the curves generated after 16 hours of soaking time gave an average SBM value of 30.43 kgf/mm and an average USBS value of 1.75 kgf. Calculation of a percent reduction of SBM and the USBS indicates more than a 40 and 78% reduction of SBM and USBS values after 6 hours soaking time relative to such values of the non-spotting fluid tests. On the other hand, calculation of a percent reduction of SBM and USBS after 16 hours soaking time indicates more than 20 and 70% reduction of SBM and the USBS, respectively. The data may, therefore, indicate that the Spotting Fluid #2 is able to reduce the SBM and USBS of the mudcakes significantly after 6 and 16 hours of soaking time. However, the tests indicate somewhat lower reduction of SBM and USBS after 16 hours soaking time versus 6 hours soaking time. This may indicate a reversal of degradation and damaging effect due to an interaction hardening effect on the sticking bonds in the presence of Spotting Fluid #2. This result may also indicate that the soaking time above an optimum soaking period has no technical benefit. For example, a longer soaking time for some spotting fluids may need result in a higher required pulling force than the pulling force required after an optimum soaking time due to the interaction hardening effect of the spotting fluid. Hence, it may be advantageous to evaluate the performance of various spotting fluids in the lab to identify the optimum soaking time for the maximum ease of recovery of a stuck pipe.

The tests curves generated after 6 hours of soaking time in the presence of Spotting Fluid #3 gave an average SBM value of 21.65 kgf/mm and an average USBS value of 0.6 kgf. However, the curves generated after 16 hours of soaking time gave an average SBM value of 23.08 kgf/mm and an average USBS value of 0.6 kgf. Calculation of a percent reduction of SBM and the USBS indicates more than 43 and 90% reduction of SBM and USBS values after 6 hours soaking time relative to such values of the non-spotting fluid tests. On the other hand, calculation of a percent reduction of SBM and USBS after 16 hours soaking time indicates more than 39 and 90% reduction of SBM and the USBS, respectively. This result indicates little or negligible reduction in the SBM and USBS after 16 hours soaking time versus 6 hours soaking time. The data may indicate that the Spotting Fluid #3 is able to reduce the SBM and USBS of the mudcakes significantly within a short time interval such as 6 hours and less. The data may further indicate that the longer soaking time has no or insignificant benefit for some spotting fluids due to their full and complete interaction potential within an optimum time. This result indicates the requirement of maximum 6 hours or less soaking time for the Spotting Fluid #3.

The Spotting Fluid #2 test results may provide certain information. First, such results may indicate a need of a shorter time of interaction between the fluid and the mudcake sample to cause damage, degradation, or weakening of sticking bonds of the mudcake-member interface. The data may also indicate that the 6 hours soaking time is enough for the Spotting Fluid #2. Second, the data may indicate the long term interaction hardening of the sticking bonds in the presence of Spotting Fluid #2. This is reflected by a higher SBM and USBS values after 16 hours of soaking time compared to 6 hours soaking time.

According to the Spotting Fluid #1 and the Spotting Fluid #2 test results, the Spotting Fluid #2 may have better performance in weakening the sticking bonds and releasing the embedded member from the mudcake sample, and thus the better spotting fluid for debonding a stuck pipe from a mudcake in a wellbore.

Data for the Spotting Fluid #3 tests, similar to the Spotting Fluid #2, may also provide information. First, such results may indicate a need of a shorter time of interactions to cause damage, degradation, or weakening of sticking bonds of the mudcake-member interface. The data may also indicate that 6 hours or less soaking time is enough for the Spotting Fluid #3 for sufficient degradation of the sticking bonds formed in the member-mudcake interface. Second, the data may indicate the absence of any long term interaction hardening effect in the presence of the Spotting Fluid #3. This is reflected by negligible changes in SBM and USBS values after 16 hours of soaking time compared to 6 hours soaking time.

Test data resulting from operations with the spotting fluid testing system 700 may be predictively used (for example, by the control system 710) to determine or help determine real-world operations. For example, the control system 710 may predict, based on test results using one or more spotting fluids, that a particular spotting fluid should be used to help unstick a drill pipe or other tubular member from a wellbore with a particular mudcake composition. For example, the control system 710 may predict, based on test results from one or more spotting fluids, that a particular spotting fluid should soak a mudcake into which a drill pipe or other tubular member is stuck for a particular time duration before attempting to free the tubular member.

Figure 11:
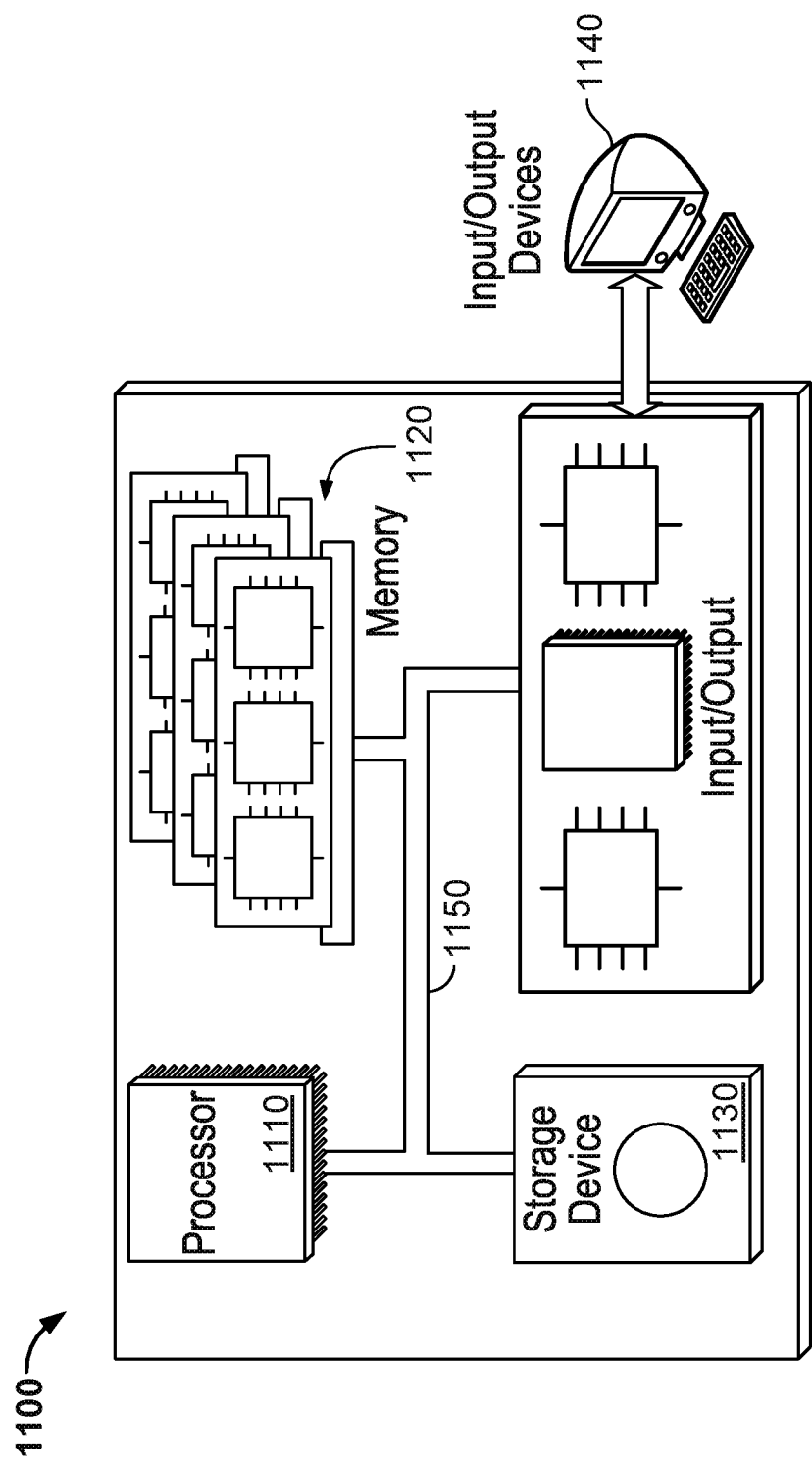
FIG. 11 illustrates a schematic diagram of a control system that can be used for the operations described in association with any of the computer-implemented methods described herein.

FIG. 11 is a schematic diagram of a control system (or controller) 1100. The system 1100 can be used for the operations described in association with any of the computer-implemented methods described previously as or as part of the control system 110, 710, or other controllers described in this disclosure. For example, the system 1100 may be used in providing local control for a mudcake testing system as shown in FIGS. 1A and 7, remote control or monitoring of a mudcake testing system (for example, for a system placed at a wellsite location), or otherwise.

The system 1100 is intended to include various forms of digital computers, such as laptops, desktops, workstations, personal digital assistants, servers, blade servers, mainframes, and other appropriate computers. The system 1100 can also include mobile devices, such as personal digital assistants, cellular telephones, smartphones, and other similar computing devices. Additionally the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device.

The system 1100 includes a processor 1110, a memory 1120, a storage device 1130, and an input/output device 1140. Each of the components 1110, 1120, 1130, and 1140 are interconnected using a system bus 1150. The processor 1110 is capable of processing instructions for execution within the system 1100. The processor may be designed using any of a number of architectures. For example, the processor 1110 may be a CISC (Complex Instruction Set Computers) processor, a RISC (Reduced Instruction Set Computer) processor, or a MISC (Minimal Instruction Set Computer) processor.

In one implementation, the processor 1110 is a single-threaded processor. In another implementation, the processor 1110 is a multi-threaded processor. The processor 1110 is capable of processing instructions stored in the memory 1120 or on the storage device 1130 to display graphical information for a user interface on the input/output device 1140.

The memory 1120 stores information within the system 1100. In one implementation, the memory 1120 is a computer-readable medium. In one implementation, the memory 1120 is a volatile memory unit. In another implementation, the memory 1120 is a non-volatile memory unit. In some implementations, the control modules herein may not include a memory module 1120.

The storage device 1130 is capable of providing mass storage for the system 1100. In one implementation, the storage device 1130 is a computer-readable medium. In various different implementations, the storage device 1130 may be a floppy disk device, a hard disk device, an optical disk device, or a tape device.

The input/output device 1140 provides input/output operations for the system 1100. In one implementation, the input/output device 1140 includes a keyboard or pointing device. In another implementation, the input/output device 1140 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, for example, in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. A processor receives instructions and data from a read-only memory or a random access memory or both. The essential elements of a computer are a processor for executing instructions and one or more memories for storing instructions and data. A computer includes, or is operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer. Additionally, such activities can be implemented via touch-screen flat-panel displays and other appropriate mechanisms.

The features can be implemented in a control system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described previously as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

A number of implementations have been described. Nevertheless, it will be understood that various modifications may be made without departing from the spirit and scope of the disclosure. For example, example operations, methods, or processes described herein may include more steps or fewer steps than those described. Further, the steps in such example operations, methods, or processes may be performed in different successions than that described or illustrated in the figures. Accordingly, other implementations are within the scope of the following claims.

What is claimed is:

1. A method, comprising:
   positioning a spherical member of a test apparatus into a prepared mudcake sample at a specified depth of the mudcake sample, the mudcake sample associated with a drilling fluid and comprising a specified thickness;
   circulating a flow of a spotting fluid to contact the prepared mudcake sample in a test cell of the test apparatus;
   soaking the prepared mudcake sample in the spotting fluid for a specified time duration;
   subsequent to the specified time duration, detecting, with the test apparatus, a force exerted on the spherical member relative to a displacement distance of the spherical member from the specified depth in the mudcake sample during removal of the spherical member from the mudcake sample;
   recording, with the test apparatus, the detected force relative to the displacement distance; and
   determining, with the test apparatus, one or more properties associated with the mudcake sample based on the recorded force relative to the displacement distance.

2. The method of claim 1, further comprising collecting an overflow of the spotting fluid that flows from the test cell.

3. The method of claim 1, wherein circulating the flow of the spotting fluid comprises circulating, by a gravity feed, the spotting fluid from a feeder tank to the test cell.

4. The method of claim 3, wherein the feeder tank is positioned vertically above the test cell.

5. The method of claim 1, wherein circulating the flow of the spotting fluid comprises circulating a pressurized flow of the spotting fluid from a feeder tank to the test cell.

6. The method of claim 5, further comprising pressurizing the spotting fluid in the feeder tank with a pressurized gas stored in a gas tank in fluid communication with the feeder tank.

7. The method of claim 6, further comprising regulating a pressure of the pressurized gas circulating from the gas tank to the feeder tank.

8. The method of claim 7, further comprising:
   maintaining, for a specified time period, the spherical member in the mudcake sample prior to circulating the spotting fluid, wherein the specified time period comprises 2 minutes;

initiating removal of the spherical member from the mudcake sample by the force exerted on the spherical member by the test apparatus, wherein the specified thickness is 10 mm and the specified depth is 5 mm;

removing the spherical member from the mudcake sample by the force exerted on the spherical member by the test apparatus, wherein removing the spherical member from the mudcake sample by the force exerted on the spherical member by the test apparatus comprises removing the spherical member from the mudcake sample at a constant removal rate.

9. The method of claim 1, further comprising initiating removal of the spherical member from the mudcake sample by the force exerted on the spherical member by the test apparatus.

10. The method of claim 1, wherein the specified thickness is 10 mm and the specified depth is 5 mm.

11. The method of claim 1, further comprising removing the spherical member from the mudcake sample by the force exerted on the spherical member by the test apparatus.

12. The method of claim 11, wherein removing the spherical member from the mudcake sample by the force exerted on the spherical member by the test apparatus comprises removing the spherical member from the mudcake sample at a constant removal rate.

13. The method of claim 1, further comprising maintaining, for a specified time period, the spherical member in the mudcake sample prior to circulating the spotting fluid.

14. The method of claim 13, wherein the specified time period comprises 2 minutes.

15. The method of claim 1, wherein one or more properties of the mudcake sample comprise a sticking bond modulus (SBM) and an ultimate sticking bond strength (USBS).

16. The method of claim 1, further comprising determining at least one of the one or more properties based, at least in part, on the graphical recording of the force exerted on the spherical member relative to the displacement distance.

17. The method of claim 1, further comprising performing an action based at least in part on the one or more of the determined properties, the action comprising at least one of:
selecting a drilling fluid to use in a drilling operation;
selecting a particular spotting fluid to use in a stuck-pipe removal operation; or
determining an ease of recovery of a tubular member that is stuck in a wellbore.

18. A spotting fluid testing system, comprising:
a test apparatus comprising:
a mudcake holder configured to restrain a mudcake sample in a stationary position;
a load cell; and
a spherical testing member coupled to the load cell; and
a control system communicably coupled to the test apparatus and configured to perform operations comprising:
controlling the load cell to position the spherical testing member into the mudcake sample at a specified depth of the mudcake sample;
controlling one or more valves of the test apparatus to circulate a flow of a spotting fluid to contact and soak the mudcake sample in a test container of the test apparatus;
subsequent to a specified soaking time duration, controlling the load cell to initiate removal of the spherical testing member from the mudcake sample by a force exerted on the spherical testing member by the load cell;
detecting, with the test apparatus, a force exerted on the spherical testing member relative to a displacement distance of the spherical testing member from the specified depth in the mudcake sample during removal of the spherical testing member from the mudcake sample;
recording, with the test apparatus, the detected force relative to the displacement distance; and
determining one or more properties of the mudcake sample based on the recorded force relative to the displacement distance.

19. The spotting fluid testing system of claim 18, further comprising a collection tank fluidly coupled to the test cell, the control system further configured to perform operations comprising:
controlling one or more valves of the test apparatus to circulate an overflow of the spotting fluid from the test cell to the collection tank.

20. The spotting fluid testing system of claim 18, further comprising a feeder tank positioned vertically above the test cell to circulate the flow of the spotting fluid from the feeder tank to the test cell by a gravity feed.

21. The spotting fluid testing system of claim 20, further comprising a gas tank that stores a pressurized gas, the gas tank fluidly coupled with the feeder tank, the control system further configured to perform operations comprising:
controlling one or more valves to circulate the pressurized gas to the feeder tank to generate a pressurized flow of the spotting fluid from the feeder tank to the test cell.

22. The spotting fluid testing system of claim 21, wherein the control system is further configured to perform operations comprising controlling a pressure regulator of the gas tank to adjust a pressure of the pressurized gas circulating from the gas tank to the feeder tank.

23. The spotting fluid testing system of claim 21, wherein the control system is further configured to perform operations comprising:
initiating removal of the spherical testing member from the mudcake sample by the force exerted on the spherical testing member by the test apparatus, wherein the specified thickness is 10 mm and the specified depth is 5 mm; and
removing the spherical testing member from the mudcake sample by the force exerted on the spherical testing member by the test apparatus, wherein removing the spherical testing member from the mudcake sample by the force exerted on the spherical testing member by the test apparatus comprises removing the spherical testing member from the mudcake sample at a constant removal rate.

24. The spotting fluid testing system of claim 18, wherein the control system is further configured to perform operations comprising initiating removal of the spherical testing member from the mudcake sample by the force exerted on the spherical testing member by the test apparatus.

25. The spotting fluid testing system of claim 18, wherein the specified thickness is 10 mm and the specified depth is 5 mm.

26. The spotting fluid testing system of claim 18, wherein the control system is further configured to perform operations comprising removing the spherical testing member from the mudcake sample by the force exerted on the spherical testing member by the test apparatus.

27. The spotting fluid testing system of claim 26, wherein removing the spherical testing member from the mudcake sample by the force exerted on the spherical testing member by the test apparatus comprises removing the spherical testing member from the mudcake sample at a constant removal rate.

28. The spotting fluid testing system of claim 18, wherein one or more properties of the mudcake sample comprise a sticking bond modulus (SBM) and an ultimate sticking bond strength (USBS).

29. The spotting fluid testing system of claim 18, wherein the control system is further configured to perform operations comprising determining at least one of the one or more properties based, at least in part, on the graphical recording of the force exerted on the spherical testing member relative to the displacement distance.

30. The spotting fluid testing system of claim 18, wherein the control system is further configured to perform operations comprising recommending an action based at least in part on the one or more of the determined properties, the action comprising at least one of:
- selecting a drilling fluid to use in a drilling operation;
- selecting a particular spotting fluid to use in a stuck-pipe removal operation; or
- determining an ease of recovery of a tubular member that is stuck in a wellbore.

* * * * *